US012742178B2

(12) United States Patent
Bowen et al.

(10) Patent No.: US 12,742,178 B2
(45) **Date of Patent: *Sep. 22, 2026**

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Arlene R. Howe, Clarkson Valley, MO (US); Kimberly M. Wegener, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 158 days.

This patent is subject to a terminal disclaimer.

(21) Appl. No.: 18/793,450

(22) Filed: Aug. 2, 2024

(65) Prior Publication Data

US 2025/0002931 A1 Jan. 2, 2025

Related U.S. Application Data

(63) Continuation of application No. 17/854,198, filed on Jun. 30, 2022, now Pat. No. 12,104,162.

(60) Provisional application No. 63/348,278, filed on Jun. 2, 2022, provisional application No. 63/219,604, filed on Jul. 8, 2021.

(51) Int. Cl.

| | |
|---|---|
| ***C12N 15/82*** | (2006.01) |
| ***A01N 63/23*** | (2020.01) |
| ***A01N 63/50*** | (2020.01) |
| ***A01P 7/04*** | (2006.01) |
| ***C07K 14/32*** | (2006.01) |

(52) U.S. Cl.

CPC ......... *C12N 15/8286* (2013.01); *A01N 63/23* (2020.01); *A01N 63/50* (2020.01); *A01P 7/04* (2021.08); *C07K 14/32* (2013.01)

(58) Field of Classification Search

None

See application file for complete search history.

(56) References Cited

U.S. PATENT DOCUMENTS

| | | | | |
|---|---|---|---|---|
| 5,188,642 | A | 2/1993 | Shah et al. | |
| 5,312,910 | A | 5/1994 | Kishore et al. | |
| 5,500,365 | A | 3/1996 | Fischhoff et al. | |
| 5,627,061 | A | 5/1997 | Barry et al. | |
| 5,633,435 | A | 5/1997 | Barry et al. | |
| 5,728,925 | A | 3/1998 | Herrera-Estrella et al. | |
| 5,880,275 | A | 3/1999 | Fischhoff et al. | |
| 6,033,874 | A | 3/2000 | Baum et al. | |
| 6,501,009 | B1 | 12/2002 | Romano | |
| 6,551,962 | B1 | 4/2003 | Pershing et al. | |
| 6,713,063 | B1 | 3/2004 | Malvar et al. | |
| 6,962,705 | B2 | 11/2005 | Malvar et al. | |
| 7,064,249 | B2 | 6/2006 | Corbin et al. | |
| 7,070,982 | B2 | 7/2006 | Malvar et al. | |
| 7,193,133 | B2 | 3/2007 | Lassner et al. | |
| 7,361,808 | B2 * | 4/2008 | Boets ................. | C12N 15/8286 435/418 |
| 7,510,878 | B2 | 3/2009 | Abad et al. | |
| 7,772,465 | B2 | 8/2010 | Abad et al. | |
| 7,812,129 | B1 | 10/2010 | Abad et al. | |
| 8,609,936 | B2 | 12/2013 | Baum et al. | |
| 12,104,162 | B2 * | 10/2024 | Bowen .................. | G01N 33/68 |
| 2004/0250313 | A1 | 12/2004 | Vincent et al. | |
| 2006/0021087 | A1 | 1/2006 | Baum et al. | |
| 2006/0112447 | A1 | 5/2006 | Bogdanova et al. | |
| 2008/0172762 | A1 | 7/2008 | Cerf et al. | |
| 2009/0313721 | A1 | 12/2009 | Abad et al. | |
| 2010/0004176 | A1 | 1/2010 | Sampson et al. | |
| 2010/0017914 | A1 | 1/2010 | Hart et al. | |
| 2010/0077507 | A1 | 3/2010 | Abad et al. | |
| 2010/0077508 | A1 | 3/2010 | Abad et al. | |
| 2010/0137216 | A1 | 6/2010 | Carozzi et al. | |
| 2010/0160231 | A1 | 6/2010 | Sampson et al. | |
| 2010/0192256 | A1 | 7/2010 | Abad et al. | |
| 2010/0197592 | A1 | 8/2010 | Heinrichs | |
| 2010/0269221 | A1 | 10/2010 | Abad et al. | |

(Continued)

FOREIGN PATENT DOCUMENTS

| | | | |
|---|---|---|---|
| EP | 0218571 | B1 | 2/1993 |
| EP | 0189707 | B1 | 8/1993 |

(Continued)

OTHER PUBLICATIONS

Palma et al, 2014, Toxins, 6:3296-3325.*
Argolo-Filho et al, 2014, Insects 5:62-91.*
Liu et al (2008, GenBank accession No. EU677422, https:// www.ncbi.nlm.nih.gov/nuccore/189039461).*
Shin et al (1995, Appl. Environ. Microbiol. 61:2402-2407).*
Alphey, et al. Combining Pest Control and Resistance Management: Synergy of Engineered Insects With Bt Crops. Journal of Economic Entomology, vol. 102, Issue 2, pp. 717-732, Apr. 1, 2009.
Della-Cioppa, et al. Translocation of the precursor of 5-enolpyruvylshikimate-3-phosphate synthase into chloroplasts of higher plants in vitro. PNAS, vol. 83, No. 18, pp. 6873-6877, (1986).

(Continued)

*Primary Examiner* — Anne Kubelik
(74) *Attorney, Agent, or Firm* — Dentons US LLP

(57) ABSTRACT

Pesticidal protein exhibiting toxic activity against Lepidopteran and Hemipteran pest species are disclosed, and include, but are not limited to, TIC2199. DNA constructs are provided which contain a recombinant nucleic acid sequence encoding the disclosed pesticidal protein. Transgenic plants, plant cells, seed, and plant parts resistant to Lepidopteran and Hemipteran infestation are provided which contain recombinant nucleic acid sequences encoding the pesticidal proteins of the present invention. Methods for detecting the presence of the recombinant nucleic acid sequences or the protein of the present invention in a biological sample, and methods of controlling Lepidopteran and Hemipteran species pests using TIC2199 pesticidal protein are also provided.

33 Claims, No Drawings

Specification includes a Sequence Listing.

(56) References Cited

U.S. PATENT DOCUMENTS

| | | | |
|---|---|---|---|
| 2010/0317569 | A1 | 12/2010 | Lira et al. |
| 2010/0319092 | A1 | 12/2010 | Lira et al. |
| 2010/0319093 | A1 | 12/2010 | Lira et al. |
| 2011/0030096 | A1 | 2/2011 | Sampson et al. |
| 2011/0055968 | A1 | 3/2011 | Cerf et al. |
| 2011/0112013 | A1 | 5/2011 | Abad et al. |
| 2011/0154536 | A1 | 6/2011 | Abad et al. |
| 2012/0047606 | A1 | 2/2012 | Abad et al. |
| 2012/0117690 | A1 | 5/2012 | Cerf et al. |
| 2012/0167259 | A1 | 6/2012 | Liu et al. |
| 2012/0192310 | A1 | 7/2012 | Abad et al. |
| 2012/0210462 | A1 | 8/2012 | Bermudez et al. |
| 2012/0233726 | A1 | 9/2012 | Abad et al. |
| 2013/0055469 | A1 | 2/2013 | Sampson et al. |
| 2013/0097735 | A1 | 4/2013 | Bowen et al. |
| 2013/0104259 | A1 | 4/2013 | Sampson et al. |
| 2013/0117884 | A1 | 5/2013 | Hargiss et al. |
| 2013/0167264 | A1 | 6/2013 | Sampson et al. |
| 2013/0219570 | A1 | 8/2013 | Lira et al. |
| 2013/0254933 | A1 | 9/2013 | Kramer |
| 2013/0269060 | A1 | 10/2013 | Baum et al. |
| 2013/0303440 | A1 | 11/2013 | Sampson et al. |
| 2013/0310543 | A1 | 11/2013 | Sampson et al. |
| 2014/0007292 | A1 | 1/2014 | Cerf et al. |
| 2014/0033361 | A1 | 1/2014 | Altier et al. |
| 2014/0033363 | A1 | 1/2014 | Sampson |
| 2014/0090104 | A1 | 3/2014 | Hart et al. |
| 2014/0196175 | A1 | 7/2014 | Sampson et al. |
| 2014/0223598 | A1 | 8/2014 | Sampson et al. |
| 2014/0223599 | A1 | 8/2014 | Sampson et al. |
| 2014/0245491 | A1 | 8/2014 | Sampson et al. |
| 2014/0298538 | A1 | 10/2014 | Heinrichs et al. |
| 2014/0366227 | A1 | 12/2014 | Gatehouse et al. |
| 2014/0373195 | A1 | 12/2014 | Sampson et al. |
| 2017/0058294 | A1 | 3/2017 | Bowen et al. |
| 2017/0367383 | A1 | 12/2017 | Esquivel et al. |
| 2018/0028512 | A1 | 2/2018 | Lee et al. |
| 2018/0094234 | A1 | 4/2018 | Lyte |
| 2018/0362598 | A1 | 12/2018 | Carlson et al. |
| 2019/0261634 | A1 | 8/2019 | Carlson et al. |
| 2024/0425872 | A1 | 12/2024 | Bowen et al. |

FOREIGN PATENT DOCUMENTS

| | | | |
|---|---|---|---|
| EP | 0508909 | B1 | 8/1998 |
| EP | 0924299 | B1 | 5/2004 |
| WO | 2013134523 | A1 | 9/2013 |
| WO | 2014008054 | A2 | 1/2014 |
| WO | 2014138339 | | 9/2014 |
| WO | 2015195594 | A2 | 12/2015 |
| WO | 2016061391 | A2 | 4/2016 |
| WO | 2016061392 | A1 | 4/2016 |

OTHER PUBLICATIONS

GenBank accession ACD75515.1, dated May 28, 2008.

ISAAA. 2016. Global Status of Commercialized Biotech/GM Crops: 2016. ISAAA Brief No. 52. ISAAA: Ithaca, NY.

Jin et al., 2013. Engineered female-specific lethality for control of pest Lepidoptera. ACS Synthetic Biology, 2: 160-166.

Klee, et al. Cloning of an *Arabidopsis thaliana* gene encoding 5-enolpyruvylshikimate-3-phosphate synthase: sequence analysis and manipulation to obtain glyphosate-tolerant plants. Mol Gen Genet 210, 437-442 (1987).

Escudero, et al. Molecular and Insecticidal Characterization of a Cry1I Protein Toxic to Insects of the Families Noctuidae, Tortricidae, Plutellidae, and Chrysomelidae. American Society for Microbiology, Applied and Environmental Microbiology, vol. 72, Issue 7, pp. 4796-4804, (2006).

Schnepf, et al. Bacillus thuringiensis and Its Pesticidal Crystal Proteins. American Society for Microbiology, Microbiology and Molecular Biology Reviews, vol. 62, Issue 3, pp. 775-806, (1998).

Thompson, et al. CLUSTAL W: improving the sensitivity of progressive multiple sequence alignment through sequence weighting, position-specific gap penalties and weight matrix choice, Nucleic Acids Research, vol. 22, Issue 22, pp. 4673-4680, Nov. 11, 1994.

Zhou, et al. Combining the high-dose/refuge strategy and self-limiting transgenic insects in resistance management—A test in experimental mesocosms. Evolutionary Applications, vol. 11, pp. 727-738, (2018).

Invitation to Pay Additional Fees regarding International Appl. No. PCT/US2022/035787, mailed Sep. 22, 2022.

International Search Report and Written Opinion regarding International Appl. No. PCT/US2022/035787, mailed Nov. 15, 2022.

Guo et al., "Protein tolerance to random amino acid change", Proc. Natl. Acad. Sci. USA, 101(25): 9205-9210, 2004.

Argôlo-Filho et al., "Bacillus thuringiensis Is an Environmental Pathogen and Host-Specificity Has Developed as an Adaptation to Human-Generated Ecological Niches", Insects, Dec. 24, 2013, 5(1):62-91.

Jurat-Fuentes et al., "Specificity determinants for Cry insecticidal proteins: Insights from their mode of action", Journal of Invertebrate Pathology, 142:5-10, 2017.

Das et al., "Structural, functional, and evolutionary analysis of Cry toxins of Bacillus thuringiensis: an in silico study", Egypt J Biol Pest Control 31, 44 (2021).

U.S. Appl. No. 18/793,457, filed Aug. 2, 2024, Bowen et al.

* cited by examiner

INSECT INHIBITORY PROTEINS

CROSS REFERENCE TO RELATED APPLICATIONS

This application is a continuation of U.S. patent application Ser. No. 17/854,198, filed Jun. 30, 2022, which claims the benefit of U.S. Provisional Patent Appl. Nos. 63/219,604, filed Jul. 8, 2021, and 63/348,278 filed Jun. 2, 2022, the specifications of each are herein incorporated by reference in their entireties.

INCORPORATION OF SEQUENCE LISTING

The file named "MONS530USC1_ST26.xml" containing a computer-readable form of the Sequence Listing was created on Jul. 3, 2024. This file is 51,559 bytes (measured in MS-Windows®), filed contemporaneously by electronic submission (using the United States Patent Office Patent Center filing system), and incorporated by reference in its entirety.

FIELD OF THE INVENTION

The invention generally relates to the field of insect inhibitory proteins. A novel class of toxin proteins are disclosed exhibiting insect inhibitory activity against agriculturally-relevant pests of crop plants and seeds, particularly Lepidopteran species of insect pests. Plants, plant parts, seed, cells including plant and microbial cells, and vectors containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, cotton, vegetables, pearl millets, pigeon pea, peanut, potato, barley, oat, fruit trees, and the like has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these factors, environmentally sustainable improvements in technology, agricultural techniques, and pest management are vital tools to expand crop production on the increasingly limited amount of arable land available for farming.

Insects, particularly insects within the order Lepidoptera, are a major cause of damage to field crops, thereby decreasing crop yields over infested areas. Lepidopteran pest species which negatively impact agriculture include, but are not limited to, Black armyworm (*Spodoptera cosmioides*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*), Cry1Fa1 resistant Fall armyworm (*Spodoptera frugiperda*), Old World bollworm (*Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Sunflower looper (*Rachiplusia nu*), Tobacco budworm (*Heliothis virescens*), Tobacco cutworm (*Spodoptera litura*, also known as cluster caterpillar), Western bean cutworm (*Striacosta albicosta*), and Velvet bean caterpillar (*Anticarsia gemmatalis*).

Historically, the intensive application of synthetic chemical insecticides was relied upon as the pest control agent in agriculture. Concerns for the environment and human health, in addition to emerging resistance issues and the fact that such pest control agents do not discriminate and target beneficial insects and other organisms as well, stimulated the research and development of biological pesticides specifically targeted to control the pests that create the crop loss. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (*Bt*) have been used as a source for pesticidal proteins since it was discovered that *Bt* strains show a high toxicity against specific insects. *Bt* strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than *Bt*, including other *Bacillus* and a diversity of additional bacterial species, such as *Brevibacillus laterosporus, Lysinibacillus sphaericus* ("*Ls*" formerly known as *Bacillus sphaericus*), *Pseudomonas* species, *Paenibacillus popilliae* and *Paenibacillus lentimorbus*. In addition, insecticidal toxins have also been identified from a variety of non-bacterial sources including ferns, arachnid venoms, and delivery in a diet of a pest of dsRNA targeting for suppression an essential gene has been identified as an effective pest management strategy.

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein(s).

The use of transgenic plants expressing insecticidal toxin proteins has been globally adapted. For example, in 2016, 23.1 million hectares were planted with transgenic crops expressing *Bt* toxins and 75.4 million hectares were planted with transgenic crops expressing *Bt* toxins stacked with herbicide tolerance traits (*ISAAA*. 2016. *Global Status of Commercialized Biotech/GM Crops:* 2016. *ISAAA Brief No.* 52. *ISAAA*: Ithaca, NY). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action or alternatively two or more different modes of toxic action (for example, a transgene encoding a dsRNA targeting an essential gene for suppression coupled with a transgene that encodes a peptide or protein toxin, both toxic to the same insect species) reduces the probability of resistance in any single target insect species. Additionally, use of self-limiting technologies such as those provided by Oxitec Ltd, when used together with the proteins of the present invention, should improve durability of the traits imparted to transgenic crops expressing proteins of the present invention (Zhou et al. 2018. Combining the high-dose/refuge strategy and self-limiting transgenic insects in resistance management—a test in experimental mesocosms. Evol Appl 11(5): 727-738; Alphey et al. 2009. Combining pest control and resistance management: synergy of engineered insects with *Bt* crops. Journal of Economic Entomology, 102:717-732).

Thus, the inventors disclose herein a novel protein from *Bacillus thuringiensis*, along with improved engineered proteins exhibiting modified amino acid sequences relative to the native toxin, and exemplary recombinant proteins, that each exhibit insecticidal activity against target Lepidopteran species, particularly against Black cutworm (*Agrotis ipsilon*), Corn carworm (*Helicoverpa zea*), Cabbage looper worm (*Trichoplusia ni*), European corn borer (*Ostrinia nubilalis*), Fall armyworm (*Spodoptera frugiperda*), Southern armyworm (*Spodoptera eridania*), Soybean looper (*Chrysodeixis includens*), Southwestern corn borer (*Diatraea grandiosella*), Velvetbean caterpillar (*Anticarsia gemmatalis*), and Western bean cutworm (*Striacosta albicosta*), as well as, the Hemipteran species Tarnished plant bug (*Lygus lineolaris*) and Ncotropical brown stink bug (*Euschistus heros*).

SUMMARY OF THE INVENTION

Disclosed herein is a novel pesticidal protein, TIC2199, which is shown to exhibit inhibitory activity against one or more pests of crop plants. The TIC2199 protein can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or pesticidal fragment thereof, wherein the pesticidal protein comprises the amino acid sequence of SEQ ID NOs:2, 4, 7, 10, 13, 15, or 17; or the pesticidal protein comprises an amino acid sequence having at least 96%, or 97%, or 98% or 99%, or about 100% amino acid sequence identity to SEQ ID NOs:2, 4, 7, 10, 13, 15, or 17; or the polynucleotide segment hybridizes under stringent hybridization conditions to a polynucleotide having the nucleotide sequence of SEQ ID NOs:1, 3, 5, 6, 8, 9, 11, 12, 14, 16, or 18. The recombinant nucleic acid molecule can comprise a sequence that functions to express the pesticidal protein in a plant, and which when expressed in a plant cell produces a pesticidally effective amount of pesticidal protein or a pesticidal fragment thereof.

In another embodiment of this application the recombinant nucleic acid molecule is present within a bacterial or plant host cell. Contemplated bacterial host cells include at least the genus of *Agrobacterium, Rhizobium, Bacillus, Brevibacillus, Escherichia, Pseudomonas, Klebsiella, Pantoea, and Erwinia*. In certain embodiments, the *Bacillus* species is a *Bacillus cereus* or *Bacillus thuringiensis*, the *Brevibacillus* is a *Brevibacillus laterosporus*, or the *Escherichia* is an *Escherichia coli*. Contemplated plant host cells include a dicotyledonous plant cell and a monocotyledonous plant cell. Contemplated plant cells further include an alfalfa, banana, barley, bean, broccoli, cabbage, brassica (e.g. canola), carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In another embodiment, the pesticidal protein exhibits activity against Lepidopteran insects, including, at least, Black cutworm (*Agrotis ipsilon*), Corn carworm (*Helicoverpa zea*), Cabbage looper worm (*Trichoplusia ni*), European corn borer (*Ostrinia nubilalis*), Fall armyworm (*Spodoptera frugiperda*), Southern armyworm (*Spodoptera eridania*), Soybean looper (*Chrysodeixis includens*), Southwestern corn borer (*Diatraea grandiosella*), Sugarcane borer (*Diatraea saccharalis*), (Velvet bean caterpillar (*Anticarsia gemmatalis*), Western bean cutworm (*Striacosta albicosta*), and Lesser cornstalk borer (*Elasmopalpus lignosellus*).

In another embodiment, the pesticidal protein exhibits activity against Hemipteran insects, including, at least, Tarnished plant bug (*Lygus lineolaris*) and Neotropical brown stink bug (*Euschistus heros*).

Also contemplated in this application are bacteria and plants and plant parts comprising a recombinant nucleic acid molecule encoding the pesticidal protein TIC2199 or fragment thereof. The recombinant molecule (e.g. construct) may comprise a heterologous promoter for expression in bacterial or plant cells of the operably linked polynucleotide segment encoding the pesticidal protein. Both dicotyledonous plants and monocotyledonous plants are contemplated. In another embodiment, the plant is further selected from the group consisting of an alfalfa, banana, barley, bean, broccoli, cabbage, brassica (e.g. canola), carrot, cassava, castor, cauliflower, celery, chickpea, Chinese cabbage, citrus, coconut, coffee, corn, clover, cotton (i.e. *Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, corn (i.e. maize) such as sweet corn or field corn, sweet gum, sweet potato, switchgrass, tea, tobacco, tomato, triticale, turf grass, watermelon, and wheat. The plant parts may for instance include, without limitation, leaves, tubers, roots, stems, seeds, embryos, flowers, inflorescences, bolls, pollen, fruit, animal feed, and biomass. Processed plant parts, for instance wood, or oil, non-viable ground seeds or fractionated seeds, flour, or starch produced from the plant leaves, flowers, roots, seeds or tubers containing the nucleic acids encoding the proteins of the present invention, and/or containing pesticidally effective amounts of the encoded toxin proteins, are also contemplated.

In certain embodiments, seeds comprising the recombinant nucleic acid molecules and pesticidally effective amounts of the TIC2199 toxin proteins, are disclosed.

In still another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. It is also contemplated that the at least one other pesticidal agent in the insect inhibitory composition exhibits activity against one or more pest species of the orders Lepidoptera, Coleoptera, or Hemiptera. The at least one other pesticidal agent in the insect inhibitory composition is, in one embodiment, selected from the group consisting of a Cry1A, Cry1Ab, Cry1Ac, Cry1A.105, Cry1Ac, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ac, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-2222, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657, DIG-11 protein, IDP102Aa and homologs thereof, IDP110Aa and homologs thereof, TIC868, Cry1Da1_7, BCW003, TIC1100, TIC867, TIC867_23, TIC6757. TIC7641, IDP072Aa, TIC5290, TIC3668, TIC3669, TIC3670, IDP072Aa and IDP103 and homologs thereof, PIP-50 and PIP-65 and homologs thereof, PIP-83 and homologs thereof, and Cry1B.34; and dsRNA mediated gene suppression embodiments including those targeting for suppression *Diabrotica* species genes Dv snf7 and Dv ssj1.

Commodity products comprising a detectable amount of the recombinant nucleic acid molecules and toxin proteins disclosed in this application are also contemplated. Such commodity products include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated in this application is a method of producing seed comprising recombinant nucleic acid molecules and pesticidally effective amounts of the encoded TIC2199 toxin protein. The method comprises planting at least one seed comprising the recombinant nucleic acid molecules disclosed in this application; growing a plant from the seed; and harvesting seed from the plant, wherein the harvested seed comprises the referenced recombinant nucleic acid molecules and/or pesticidally effective amounts of the encoded TIC2199 toxin protein.

In another illustrative embodiment, a plant resistant to Lepidopteran insect infestation, is provided wherein the cells of said plant comprise the recombinant nucleic acid molecules disclosed herein.

Also disclosed in this application are methods for controlling a Lepidopteran species pest and controlling a Lepidopteran species pest infestation of a plant, particularly a crop plant. The method comprises, in one embodiment, first contacting the pest with an insecticidally effective amount of a pesticidal protein as set forth in SEQ ID NOs:2, 4, 7, 10, 13, 15, or 17; or contacting the pest with an insecticidally effective amount of one or more pesticidal proteins comprising an amino acid sequence having at least 96%, or 97%, or 98% or 99%, or about 100% amino acid sequence identity to SEQ ID NOs:2, 4, 7, 10, 13, 15, or 17.

Further provided herein is a method of detecting the presence of a recombinant nucleic acid molecule of the TIC2199 toxin protein class wherein the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NOs:3, 6, 9, 12, 14, 16, or 18, or a sequence that encodes a pesticidal protein comprising an amino acid sequence having at least 96%, or 97%, or 98% or 99%, or about 100% amino acid sequence identity to SEQ ID NOs:2, 4, 7, 10, 13, 15, or 17; subjecting the sample and probe to stringent hybridization conditions; and detecting hybridization of the probe with DNA of the sample. In some embodiments a step of detecting the presence of a member of the TIC2199 toxin protein class may comprise an ELISA or a western blot.

Also provided herein are methods of detecting the presence of the pesticidal protein or fragment thereof from the TIC2199 toxin protein class wherein the method comprises contacting a sample with a TIC2199 toxin protein class immunoreactive antibody or recombinant protein designed for detecting the TIC2199 protein, and detecting the binding of the antibody to the TIC2199 toxin protein class protein, thus confirming the presence of the protein in the sample. In some embodiments the step of detecting comprises an ELISA, or a Western blot.

Also contemplated in this application is a method for controlling a Lepidopteran pest species or pest infestation in a field wherein the method comprises growing a crop plant which expresses an insecticidally effective amount of a pesticidal protein as set forth in SEQ ID NOs:2, 4, 7, 10, 13, 15, or 17; or growing a crop plant which expresses an insecticidally effective amount of one or more pesticidal proteins comprising an amino acid sequence having at least 96%, or 97%, or 98%, or 99%, or about 100% amino acid sequence identity to SEQ ID NOs:2, 4, 7, 10, 13, 15, or 17; and releasing into the field with crops containing a gene encoding the toxin protein of the present invention, one or more transgenic Lepidopteran pest species each carrying a self-limiting gene, for the purpose of preventing or delaying the onset of resistance of the one or more Lepidopteran pest species to the toxin protein. In one embodiment, the crop plants can be monocotyledonous or dicotyledonous. In another embodiment, the monocotyledonous crop plants can be corn, wheat, sorghum, rice, rye, or millet. In yet another embodiment, the dicotyledonous crop plant can be soybean, cotton, or canola.

BRIEF DESCRIPTION OF THE SEQUENCES

SEQ ID NO:1 is a nucleic acid sequence encoding a TIC2199 pesticidal protein obtained from *Bacillus thuringiensis* species EG8639.

SEQ ID NO:2 is the amino acid sequence of the TIC2199 pesticidal protein encoded by the sequence set forth in SEQ ID NO:1.

SEQ ID NO:3 is a synthetic coding sequence encoding TIC2199 and capable of use in a plant cell.

SEQ ID NO:4 is an amino acid sequence of a variant of TIC2199, TIC2199_3 in which the N-terminal 44 amino acids comprising a secretion peptide have been removed, and the C-terminal 64 amino acids are also removed.

SEQ ID NO:5 is a DNA sequence encoding the TIC2199_3 variant of SEQ ID NO:4.

SEQ ID NO:6 is a synthetic coding sequence encoding the TIC2199_3 variant of SEQ ID NO:4 and capable of use in a plant cell.

SEQ ID NO:7 is an amino acid sequence of a variant of TIC2199, TIC2199_1 in which the N-terminal 44 amino acids comprising a secretion peptide have been removed.

SEQ ID NO:8 is a DNA sequence encoding the TIC2199_1 variant of SEQ ID NO:7.

SEQ ID NO:9 is a synthetic coding sequence encoding the TIC2199_1 variant of SEQ ID NO: 7 and capable of use in a plant cell.

SEQ ID NO:10 is an amino acid sequence of a variant of TIC2199, TIC2199_2 in which the C-terminal 64 amino acids are also removed.

SEQ ID NO:11 is a DNA sequence encoding the TIC2199_2 variant of SEQ ID NO: 10.

SEQ ID NO:12 is a synthetic coding sequence encoding the TIC2199_2 variant of SEQ ID NO: 10 and capable of use in a plant cell.

SEQ ID NO:13 is an amino acid sequence of the variant TIC2199_1 variant with the initiating methionine removed and used to operably link to a chloroplast transit peptide.

SEQ ID NO:14 is a synthetic coding sequence encoding the TIC2199_1 variant with the initiating methionine codon removed and used to operably link to a chloroplast transit peptide, and capable of use in a plant cell.

SEQ ID NO:15 is an amino acid sequence of the variant TIC2199_2 variant with the initiating methionine removed and used to operably link to a chloroplast transit peptide.

SEQ ID NO:16 is a synthetic coding sequence encoding the TIC2199_2 variant with the initiating methionine codon removed and used to operably link to a chloroplast transit peptide, and capable of use in a plant cell.

SEQ ID NO: 17 is an amino acid sequence of the variant TIC2199_3 variant with the initiating methionine removed and used to operably link to a chloroplast transit peptide.

SEQ ID NO:18 is a synthetic coding sequence encoding the TIC2199_3 variant with the initiating methionine codon removed and used to operably link to a chloroplast transit peptide, and capable of use in a plant cell.

DETAILED DESCRIPTION OF THE INVENTION

One problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

A novel pesticidal protein exemplified by TIC2199 is disclosed herein. Use of the protein in pesticidally effective amounts can address insect infestation that are problems in the art, particularly against a broad spectrum of Lepidopteran insect pests, and more particularly against Black cutworm (*Agrotis ipsilon*), Corn carworm (*Helicoverpa zea*), Cabbage looper worm (*Trichoplusia ni*), European corn borer (*Ostrinia nubilalis*), Fall armyworm (*Spodoptera frugiperda*), Southern armyworm (*Spodoptera eridania*), Soybean looper (*Chrysodeixis includens*), Southwestern corn borer (*Diatraea grandiosella*), Velvetbean caterpillar (*Anticarsia gemmatalis*), and Western bean cutworm (*Striacosta albicosta*), as well as against the Hemipteran species Tarnished plant bug (*Lygus lineolaris*) and Neotropical brown stink bug (*Euschistus heros*).

Reference in this application to TIC2199, "TIC2199 protein", "TIC2199 protein toxin", "TIC2199 pesticidal protein", "TIC2199-related toxins", "TIC2199-related toxins", "TIC2199 protein toxin class", "TIC2199 toxin protein class" and the like, refer to any novel pesticidal protein or insect inhibitory protein, that comprises, that consists of, that is substantially homologous to, that is similar to, or that is derived from any pesticidal protein or insect inhibitory protein sequence of TIC2199 (SEQ ID NO:2), and pesticidal or insect inhibitory segments thereof, or combinations thereof, that confer activity against Lepidopteran pests, including any protein exhibiting pesticidal or insect inhibitory activity if alignment of such protein with TIC2199 results in an amino acid sequence of identity of any fraction percentage form about 96% to about 100% percent. The TIC2199 proteins include both the plastid-targeted and non-plastid targeted form of the proteins.

The term "segment" or "fragment" is used in this application to describe consecutive amino acid or nucleic acid sequences that are shorter than the complete amino acid or nucleic acid sequence describing a TIC2199 protein. A segment or fragment exhibiting insect inhibitory activity is also disclosed in this application if alignment of such segment or fragment, with the corresponding section of the TIC2199 protein set forth in SEQ ID NO:2, results in amino acid sequence identity of any fraction percentage from about 96% to about 100% between the segment or fragment and the corresponding segment of amino acids within the TIC2199 protein. A fragment as described herein may comprise at least 50, at least 100, at least 250, at least 400, at least 500, at least 600, or at least 800 contiguous amino acid residues of the TIC2199 proteins. For example, a fragment of SEQ ID NO:2 is presented as SEQ ID NO:4. The amino acid sequence of SEQ ID NO:4 comprises Domains I, II, and III of TIC2199. The proposed secretion signal peptide N-terminal 44 amino acids have been removed based upon alignment with other Cry1I pesticidal proteins (Ruiz de Escudero et al. 2006. Molecular and Insecticidal Characterization of a Cry1I Protein Toxic to Insects of the Families Noctuidae, Tortricidae, Plutellidae, and Chrysomelidae. Applied and Environmental Microbiology, 72(7):4796-4804), reserving the N terminal methionine residue. In addition, a predicted trypsin-cleaved Carboxy-terminal protoxin domain has also been removed in SEQ ID NO:4. The trypsin cleavage site is predicted as being the first lysine (K) after the "DRIEF" sequence which is highly conserved at the end of Domain III, block 5 near the start of the protoxin domain (Schnepf et al. 1998. *Bacillus thuringiensis* and Its Pesticidal Crystal Proteins. Microbiol. Mol. Biol. Rev. 62(3):775-806). SEQ ID NO:4 can be encoded for example, by SEQ ID NO:5 for expression in bacteria, or by SEQ ID NO:6 for expression in a plant cell.

In addition, a fragment of SEQ ID NO:2 is presented as SEQ ID NO:7. The amino acid of SEQ ID NO:7 comprises Domains I, II, and III of TIC2199. The proposed secretion signal peptide N-terminal 44 amino acids have been removed based upon alignment with other Cry1I pesticidal proteins. SEQ ID NO:7 can be encoded for example, by SEQ ID NO:8 for expression in bacteria, or by SEQ ID NO:9 for expression in a plant cell. A fragment of SEQ ID NO:2 is presented as SEQ ID NO:10. SEQ ID NO:10 comprises Domains I, II, and III of TIC2199. The predicted trypsin-cleaved Carboxy-terminal protoxin domain has also been removed in SEQ ID NO:10. SEQ ID NO:10 can be encoded for example, by SEQ ID NO:11 for expression in bacteria, or by SEQ ID NO:12 for expression in a plant cell. A fragment of SEQ ID NO:2 is presented as SEQ ID NO:13. The amino acid of SEQ ID NO: 13 comprises Domains I, II, and III of TIC2199. The proposed secretion signal peptide N-terminal 44 amino acids have been removed based upon alignment with other Cry1I pesticidal proteins and lacks the initiating methionine. SEQ ID NO:13 is used to operably link the TIC2199_1 amino acid sequence to a chloroplast transit peptide. SEQ ID NO:13 is encoded by SEQ ID NO:14 for expression in a plant cell. A fragment of SEQ ID NO:2 is presented as SEQ ID NO:15. The amino acid of SEQ ID NO:15 comprises Domains I, II, and III of TIC2199. The predicted trypsin-cleaved Carboxy-terminal protoxin domain has also been removed in SEQ ID NO:15 along with the initiating methionine and is used to operably link the TIC2199_2 amino acid sequence to a chloroplast transit peptide. SEQ ID NO:15 is encoded by SEQ ID NO:16 for expression in a plant cell. The amino acid of SEQ ID NO:17 comprises Domains I, II, and III of TIC2199. The proposed secretion signal peptide N-terminal 44 amino acids have been removed based upon alignment with other Cry1I pesticidal proteins and the predicted trypsin-cleaved Carboxy-terminal protoxin domain has also been removed in SEQ ID NO:17 along with the initiating methionine and is used to operably link the TIC2199_3 amino acid sequence to a chloroplast transit peptide.

Reference in this application to the terms "active" or "activity", "pesticidal activity" or "pesticidal" or "insecticidal activity", "insect inhibitory", "pesticidally effective" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop) containing an effective amount of the TIC2199 protein or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopterans, as well as protein toxins that are used to control other plant pests such as Cry, Vip, and Cyt proteins, Pseudomonas insect toxic proteins, and insect toxin proteins derived from fern species, that are available in the art for use in controlling Coleopteran, Hemipteran and Homopteran species.

It is intended that reference to a pest, particularly a pest of a crop plant, means insect pests of crop plants, particularly those Lepidoptera insect pests that are controlled by the TIC2199 protein toxin class. However, reference to a pest can also include Coleopteran, Hemipteran (for example, Tarnished plant bug (*Lygus lineolaris*)) and Neotropical brown stink bug (*Euschistus heros*) and Homopteran insect pests of plants, as well as nematodes and fungi when toxic agents targeting these pests are co-localized or present together with the TIC2199 protein or a protein that is 95 to about 100 percent identical to TIC2199 protein. The phrases "present together" or "co-localized" are intended to include any instance of which a target insect pest has been contacted by a TIC2199 toxin protein as well as any other toxic agent also present in a pesticidally effective amount relative to the target insect pest. "Contacted" is intended in certain embodiments to refer to being present in the diet of the target pest, and the diet is consumed by the target pest.

The insects of the order Lepidoptera include, but are not limited to, armyworms, cutworms, loopers, and heliothines in the Family Noctuidae, e.g., Fall armyworm (*Spodoptera frugiperda*), Beet armyworm (*Spodoptera exigua*), Black armyworm (*Spodoptera cosmioides*), Southern armyworm (*Spodoptera eridania*), bertha armyworm (*Mamestra configurata*), black cutworm (*Agrotis ipsilon*), cabbage looper worm (*Trichoplusia ni*), Sugarcane borer (*Diatraea saccharalis*), soybean looper (*Pseudoplusia includens*), Sunflower looper (*Rachiplusia nu*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), Sunflower looper (*Rachiplusia nu*), South American podworm (*Helicoverpa gelotopoeon*) western cutworm (*Agrotis orthogonia*); borers, casebearers, webworms, coneworms, cabbageworms and skeletonizers from the Family Pyralidae, e.g., European corn borer (*Ostrinia nubilalis*), navel orange worm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other Archips species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), surgarcane borer (*Diatraea saccharalis*), spiny bollworm (*Earias insulana*), spotted bollworm (*Earias vittella*), American bollworm (*Helicoverpa armigera*), corn carworm (*Helicoverpa zea*, also known as soybean podworm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), beet armyworm (*Spodoptera exigua*), tobacco cutworm (*Spodoptera litura*, also known as cluster caterpillar), and tomato leaf miner (*Tuta absoluta*).

The insects of the order Hemiptera include, but are not limited to, Stink Bugs of the family Pentatomidae: Green Stink Bugs from the genus *Chinavia* (*Chinavia hilaris, Chinavia marginata*, and *Chinavia pensylvanica*), Stink bugs of the genus *Chlorochroa* (*Chlorochroa granulose, Chlorochroa kanei, Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia*, and *Chlorochroa senilis*), Southern Green Stink Bug (*Nezara viridula*), Stink Bugs from the genus *Edessa* (*Edessa meditabunda, Edessa bifida*, and *Edessa florida*), the Neotropical Brown Stink Bug (*Euschistus heros*), stink bugs from the genus *Euschistus* (*Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus quadrator, Euschistus sevus, Euschistus strenuous, Euschistus tristigmus*, and *Euschistus variolarius*), Brown Marmorated Stink Bug (*Halyomorpha halys*), Red-Shouldered Stink Bug (*Thyanta accerra*), stink bugs of the genus *Thyanta* (*Thyanta calceata, Thyanta custator, Thyanta pallidovirens, Thyanta perditor, Thyanta maculate*, and *Thyanta pseudocasta*), the Green Belly Stink Bug (*Dichelops melacanthus*) and other stink bugs of the genus *Dichelops* (*Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix*, and *Dichelops saltensis*), the Red Banded Stink Bug (*Piezodorus guildinni*) as well as *Piezodorus lituratus*; and insects of the family of Plataspidae such as Kudzu Bug (*Megacopta cribraria*), Western tarnished plant bug (*Lygus hesperus*), and Tarnished plant bug (*Lygus lineolaris*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

Reference in this application to the term "self-limiting gene" refers to a gene that limits survival of the host, resulting in a reduction in the host population. Such technology is offered by Oxitech Ltd. Transgenic male insects carrying a transgenic self-limiting gene are released and reproduce with wild females. As a result, the progeny inherit a copy of the self-limiting gene. The self-limiting gene disrupts the proper functioning of the insects' cells by over-producing a protein in them, interfering with the cells' ability to produce other essential proteins needed for development. By disrupting the insect's normal development, the gene prevents it from surviving to adulthood. For example, the self-limiting Diamondback Moth (*Plutellidae xylostella*) strain OX4319L was developed by Oxitech Ltd and carries a male-selecting gene that utilizes sequences from the sex determination gene doublesex (dsx). The gene expresses sex-alternate splicing, to engineer female-specific expression of the self-limiting gene which prevents survival of female offspring beyond the larval stage and allows for production of male only cohorts of self-limiting moths. After being released, males mate with pest females, leading to a reduction in the number of female offspring in the next generation, thereby locally suppressing *P. xylostella* populations. To facilitate the rearing of large numbers of males for release within diamondback moth production facilities, the expression of female-specific dsx within the OX4319L strain is repressed by the addition of tetracycline, or suitable analogs, into the larval feed. OX4319L also expresses the fluorescent protein, DsRed, to permit the effective monitoring of the presence of this strain in the field (Jin et al., 2013. Engineered female-specific lethality for control of pest Lepidoptera. ACS Synthetic Biology, 2:160-166). This technology, when applied in the field with plants containing the toxin genes of the present invention, can delay or prevent the onset of resistance of pest species targeted for control by the toxin genes and proteins of the present invention, thus giving a greater durability of any plant product containing the toxin genes and proteins of the present invention.

As described further in this application, an open reading frame (ORF) encoding TIC2199 (SEQ ID NO:1) was discovered in DNA obtained from *Bacillus thuringiensis* species EG8639. Bioassay using microbial host cell-derived proteins of TIC2199 demonstrated activity against the Lepidopteran species Black cutworm (BCW, *Agrotis ipsilon*), Corn carworm (CEW, *Helicoverpa zea*), Cabbage looper worm (CLW, *Trichoplusia ni*), European corn borer (ECB, *Ostrinia nubilalis*), Fall armyworm (FAW, *Spodoptera frugiperda*), Southern armyworm (SAW, *Spodoptera eridania*), Soybean looper (SBL, *Chrysodeixis includens*), Southwestern corn borer (SWC, *Diatraea grandiosella*), Sugarcane borer (SCB, *Diatraea saccharalis*), Velvetbean caterpillar (VBC, *Anticarsia gemmatalis*), and Western bean cutworm (WBC, *Striacosta albicosta*), as well as, the Hemipteran species Tarnished plant bug (TPB, *Lygus lineolaris*) and Neotropical brown stink bug (NBSB, *Euschistus heros*).

Synthetic coding sequences designed for use in a plant cell were produced to express TIC2199 (SEQ ID NO:3), TIC2199_1 (SEQ ID NOs:9 and 14), TIC2199_2 (SEQ ID NOs:12 and 16), and TIC2199_3 (SEQ ID NOs:6 and 18), particularly when operationally/functionally linked to a plant functional promoter and other elements that function in plants to mediate the desired level and spatial properties for expression of the protein. Corn plants expressing TIC2199, TIC2199_1, TIC2199_2, and TIC2199_3 demonstrated efficacious activity against the Lepidopteran species European corn borer (ECB, *Ostrinia nubilalis*) and Southwestern corn borer (SWC, *Diatraea grandiosella*). In Brazil, corn plants expressing TIC2199 were efficacious against SCB and highly efficacious against LCSB.

For expression in plant cells, the TIC2199 (SEQ ID NOs:2, 4, 7, 10, 13, 15, or 17) protein can be expressed and localized in the cytosol or targeted to various organelles of the plant cell. For example, targeting a protein to the chloroplast may result in increased levels of expressed protein in a transgenic plant while preventing off-phenotypes from occurring if the expressed protein toxin reacts with the cell biology in any unexpected manner. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids in length. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated CTPs include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the TIC2199 toxin protein to the chloroplast, a sequence encoding a chloroplast transit peptide is placed 5' in operable linkage and in frame to a synthetic coding sequence encoding the TIC2199 toxin protein that has been designed for expression in plant cells.

It is contemplated that additional toxin protein sequences related to TIC2199 can be created using the amino acid sequence of TIC2199 to create novel proteins with novel properties. The TIC2199 toxin protein can be aligned to combine differences at the amino acid sequence level into novel amino acid sequence variants and making appropriate changes to the recombinant nucleic acid sequence encoding variants.

It is contemplated that improved variants of the TIC2199 protein toxin class can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence may be altered to engineer a new protein amino acid sequence. Alternatively, a fragment within the coding sequence may be replaced or deleted, or additional DNA fragments are inserted into the coding sequence, to engineer a new toxin coding sequence. The new coding sequence can encode a toxin protein with new properties such as increased activity or spectrum against insect pests, as well as provide activity against one or more insect pest species wherein resistance has developed or likely to arise against the original insect toxin protein. The plant cell comprising the gene edited toxin coding sequence can be used by methods known in the art to generate whole plants expressing the new toxin protein.

It is also contemplated that fragments of TIC2199 or protein variants thereof can be truncated forms wherein one or more amino acids are deleted from the N-terminal end, C-terminal end, the middle of the protein, or combinations thereof wherein the fragments and variants retain insect inhibitory activity. These fragments can be naturally occurring or synthetic variants of TIC2199 or derived protein variants but should retain the insect inhibitory activity of at least TIC2199.

Proteins that resemble the TIC2199 protein can be identified and compared to each other using various computer-based algorithms known in the art. Amino acid sequence identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment and are contemplated herein.

It is intended that a protein exhibiting insect inhibitory activity against a Lepidopteran insect species is related to TIC2199 if the protein is used in a query, e.g., in a Clustal W alignment, and the proteins of the present invention as set forth as SEQ ID NOs:2 or 4 are identified as hits in such alignment in which the query protein exhibits at least 96% to about 100% amino acid identity along the length of the query protein that is about 96%, 97%, 98%, 99%, 100%, or any fraction percentage in this range.

In addition to percent identity, TIC2199 and variants of TIC2199 can also be related by primary structure (conserved amino acid motifs), by length and by other characteristics. Characteristics of the TIC2199 and variants of TIC2199 protein toxin are reported in Table 1.

TIC2199 and demonstrate pesticidal activity through bioassays performed in the presence of Lepidopteran pest larvae using plant leaf disks obtained from the transformed plants. Plants can be derived from the plant cells by regeneration, seed, pollen, or meristem transformation techniques. Methods for transforming plants are known in the art.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cas12a). For methods using RNA-guided site-specific nucleases (e.g., Cas9 or Cas 12a), the recombinant DNA construct(s) will also comprise a sequence encoding one or more guide RNAs to direct the nuclease to the desired site within the plant genome.

TABLE 1

Selected characteristics of TIC2199 toxin protein.

| Protein | Molecular Weight (in Daltons) | Amino Acid Length | Isoelectric Point | Charge at PH 7.0 | No. of Hydrophobic Amino Acids | No. of Polar Amino Acids | No. of Strongly Basic (—) Amino Acids | No. of Strongly Acidic Amino Acids |
|---|---|---|---|---|---|---|---|---|
| TIC2199 | 81338.45 | 719 | 7.1197 | 5.0 | 366 | 353 | 84 | 71 |
| TIC2199_1 | 76323.99 | 675 | 7.0546 | 4.5 | 350 | 325 | 78 | 66 |
| TIC2199_2 | 73702.01 | 655 | 8.3151 | 9.5 | 337 | 318 | 75 | 58 |
| TIC2199_3 | 68687.34 | 611 | 8.4697 | 9.0 | 321 | 290 | 69 | 53 |

As described further in the Examples of this application, a synthetic nucleic acid molecule sequence encoding TIC2199 and variants of TIC2199 were designed for use in plants, encoded by SEQ ID NOs:3, 6, 9, 12, 14, 16, and 18. In view of the redundancy of the genetic code, it is within the skill of the art to produce any number of other sequences for encoding the toxin proteins however, it is understood that the sequences produced for expression in planta should avoid known problems in the art that hinder or limit the efficient expression of the coding sequence, particularly as described in U.S. Pat. No. 5,500,365.

Expression cassettes and vectors containing a recombinant nucleic acid sequence molecule can be constructed and introduced into plants, particularly such as corn, soybean, or cotton plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane) all of which are incorporated herein by reference in their entirety. Transformed cells can be regenerated into transformed plants that express Recombinant nucleic acid molecule compositions that encode bacterial and plant expressed TIC2199 proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to a TIC2199 protein encoding sequence for expression of the protein in plants or a *Bt*-functional promoter operably linked to a TIC2199 protein encoding sequence for expression of the protein in a *Bt* bacterium or other *Bacillus* species. Other elements can be operably linked to the TIC2199 protein encoding sequence including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NOs:1, 3, 5, 6, 8, 9, 11, 12, 14, 16, or 18 that encodes TIC2199 or truncated variants of TIC2199 or a protein having the amino acid sequence as set forth in SEQ ID NOs:2, 4, 7, 10, 13, 15, or 17. A heterologous promoter can also be operably linked to synthetic DNA coding sequences encoding a plastid targeted TIC2199. The codons of a recombinant nucleic acid molecule encoding for proteins disclosed herein can be substituted by synonymous codons (known in the art as a silent substitution).

A recombinant DNA construct comprising TIC2199 protein encoding sequences can further comprise a region of DNA that encodes for one or more insect inhibitory agents which can be configured to concomitantly express or co-express with a DNA sequence encoding a TIC2199 protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecule is under separate promoter control or some combination thereof. The protein of this invention can be expressed from a multi-gene expression system in which TIC2199 is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked or linked expression cassettes, each cassette expressing a different protein or other agent such as one or more dsRNA molecules.

Recombinant polynucleotides or recombinant DNA constructs comprising a TIC2199 protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC2199 protein encoding sequence in a host cell, or subsequent expression of the encoded polypeptide. An exogenous recombinant polynucleotide or recombinant DNA construct that comprises a TIC2199 protein encoding sequence and that is introduced into a host cell is referred in this application as a “transgene”.

Transgenic bacteria, transgenic plant cells, transgenic plants, and transgenic plant parts that contain a recombinant polynucleotide that expresses TIC2199 or a related family toxin protein encoding sequence are provided herein. The term “bacterial cell” or “bacterium” can include, but is not limited to, an *Agrobacterium*, a *Bacillus*, an *Escherichia*, a *Salmonella*, a *Pseudomonas, Brevibacillus, Klebsiella, Erwinia*, or a *Rhizobium* cell. The term “plant cell” or “plant” can include but is not limited to a dicotyledonous or monocotyledonous plant. The term “plant cell” or “plant” can also include but is not limited to an alfalfa, banana, barley, bean, broccoli, cabbage, brassica (e.g. canola), carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, corn (i.e. maize, such as sweet corn or field corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a “non-regenerable” portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Lepidoptera-inhibitory or Hemipteran-inhibitory amounts of a TIC2199 protein are provided. Such plants can be made by introducing a recombinant polynucleotide that encodes any of the proteins provided in this application into a plant cell, and selecting a plant derived from said plant cell that expresses an insect, Lepidoptera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC2199, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC2199.

Plants expressing the TIC2199 protein can be crossed by breeding with transgenic events expressing other toxin proteins and/or expressing other transgenic traits such as herbicide tolerance genes, genes conferring yield or stress tolerance traits, and the like, or such traits can be combined in a single stacked vector so that the traits are all linked.

As further described in the Examples, TIC2199 protein-encoding sequences and sequences having a substantial percentage identity to TIC2199, can be identified using methods known to those of ordinary skill in the art such as polymerase chain reaction (PCR), thermal amplification, and hybridization. For example, the proteins TIC2199 can be used to produce antibodies that bind specifically to related proteins and can be used to screen for and to find other protein members that are closely related.

Furthermore, nucleotide sequences encoding the TIC2199 toxin protein can be used as probes and primers for screening to identify other members of the class using thermal-cycle or isothermal amplification and hybridization methods. For example, oligonucleotides derived from sequences as set forth in SEQ ID NOs:3, 6, 9, or 12 can be used to determine the presence or absence of a TIC2199 transgene in a deoxyribonucleic acid sample derived from a commodity product. Given the sensitivity of certain nucleic acid detection methods that employ oligonucleotides, it is anticipated that oligonucleotides derived from sequences as set forth in SEQ ID NO:3 can be used to detect a TIC2199 transgene in commodity products derived from pooled sources where only a fraction of the commodity product is derived from a transgenic plant containing any of the transgenes. It is further recognized that such oligonucleotides can be used to introduce nucleotide sequence variation in each of SEQ ID NOs:1, 3, 5, 6, 8, 9, 11, 12, 14, 16, and 18. Such “mutagenesis” oligonucleotides are useful for identification of TIC2199 amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be any of the nucleotide sequences presented as of SEQ ID NOs:1, 3, 5, 6, 8, 9, 11, 12, 14, 16, or 18 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* sequences encoding TIC2199 variants. This application contemplates the use of these, and other identification methods known to those of ordinary skill in the art, to identify TIC2199 variant protein-encoding sequences and sequences having a substantial percentage identity to TIC2199 variants protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC2199 protein to derive additional useful embodiments including assembly of segments of TIC2199 protein with segments of diverse proteins different from TIC2199 protein and related proteins. The TIC2199 protein may be subjected to alignment to each other and to other *Bacillus, Paenibacillus* or other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera infestations of crop plants, with the TIC2199 protein are disclosed in this application. Such methods can comprise growing a plant comprising an insect- or Lepidoptera-inhibitory amount of a TIC2199 toxin protein. In certain embodiments, such methods can further comprise any one or more of: (i) applying any composition comprising or encoding a TIC2199 toxin protein to a plant or a seed that gives rise to a plant; and (ii) transforming a plant or a plant cell that gives rise to a plant with a polynucleotide encoding a TIC2199 toxin protein. In general, it is contemplated that a TIC2199 toxin protein can be provided in a composition, provided in a microorganism, or provided in a transgenic plant to confer insect inhibitory activity against Lepidopteran insects.

In certain embodiments, a recombinant nucleic acid molecule of TIC2199 toxin protein is the insecticidally active ingredient of an insect inhibitory composition prepared by culturing recombinant *Bacillus* or any other recombinant bacterial cell transformed to express a TIC2199 toxin protein under conditions suitable to express the TIC2199 toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC2199 protein can further comprise at least one additional polypeptide that exhibits insect inhibitory activity against the same Lepidopteran insect species, but which is different from the TIC2199 toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ac, Cry1B (U.S. patent Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication n WO2016/061391 (A2)), TIC2160 (International Application Publication WO2016/061392 (A2)), Cry2A, Cry2Ab (U.S. Pat. No. 7,064,249), Cry2Ac, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523 (A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594 A2), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NOs:2 or 4 and derivatives thereof as described in U.S. Patent Publication 2012-0167259 A1, 2SEQ ID NO:2 or 4 and derivatives thereof as described in U.S. Patent Publication 2012-0047606 A1, SEQ ID NOs:2 or 4 and derivatives thereof as described in U.S. Patent Publication 2011-0154536 A1, SEQ ID NOs:2 or 4 and derivatives thereof as described in U.S. Patent Publication 2011-0112013 A1, SEQ ID NOs:2 or 4 and 4 and derivatives thereof as described in U.S. Patent Publication 2010-0192256 A1, SEQ ID NOs:2 or 4 and derivatives thereof as described in U.S. Patent Publication 2010-0077507 A1, SEQ ID NOs:2 or 4 and derivatives thereof as described in U.S. Patent Publication 2010-0077508 A1, SEQ ID NOs:2 or 4 and derivatives thereof as described in U.S. Patent Publication 2009-0313721 A1, SEQ ID NOs:2 or 4 and derivatives thereof as described in U.S. Patent Publication 2010-0269221 A1, SEQ ID NOs:2 or 4 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NOs:2 or 4 and derivatives thereof as described in U.S. Pat. No. 7,510,878 (B2), SEQ ID NOs:2 or 4 and derivatives thereof as described in U.S. Pat. No. 7,812,129 (B1); and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Further a polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), CHIPs (U.S. Patent Application Publication No. 2010/0017914), IP3 and variants thereof (U.S. Patent Publication 2012-0210462 A1), and ω-Hexatoxin-Hv1a (U.S. Patent Application Publication US2014-0366227 A1).

Additional polypeptides for the control of Coleopteran, Lepidopteran, and Hemipteran insect pests, which can be combined with the insect inhibitory proteins of the TIC2199 class, can be found on the *Bacillus thuringiensis* toxin nomenclature website maintained by Neil Crickmore (on the world wide web at btnomenclature.info). Broadly, it is contemplated that any insect inhibitory protein known to those of ordinary skill in the art can be used in combination with the proteins of the TIC2199 family both in planta (combined through breeding or molecular stacking) or in a composition or formulation as a biopesticide or combination of biopesticides.

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC2199 pesticidal protein.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

Example 1

Discovery, Cloning, and Expression of TIC2199

The TIC2199 pesticidal protein was identified through sequence analysis of the genome of the *Bacillus thuringiensis* (*Bt*) strain EG8639. *Bt* strain EG8639 was initially identified as a spore forming, crystal and plasmid containing strain of *Bt* or *Bt*-like bacteria. DNA was isolated from EG8639 and sequenced. The assembled sequence was then analyzed bioinformatically. The TIC2199 protein was identified by pfam analysis to hits of endotoxin domains and identity to a known Cry1Ib3 toxin, GenBank accession ACD75515. The full length TIC2199 protein amino acid sequence exhibits 95.13% identity to the amino acid sequence of the CryIb3 protein of GenBank accession ACD75515.

Polymerase chain reaction (PCR) primers were designed to amplify a full-length copy of the coding region for TIC2199 from total genomic DNA isolated from the *Bt* strain, EG8639. The PCR amplicons were cloned using methods known in the art into two plasmid constructs: one into an *Escherichia coli* (*Ec*) expression vector in operable linkage with an *Ec* expressible promoter and a histidine tag used for protein purification; and the other into a *Bt* expression vector in operable linkage with a *Bt* expressible promoter. Preparations of TIC2199 derived from both *Ec* and *Bt* were used in bioassay.

Example 2

TIC2199 Demonstrated Lepidopteran Activity in Insect Bioassay

The pesticidal protein TIC2199 was expressed in recombinant *Ec* and *Bt* using the vectors described in Example 1, and the resulting proteins expressed in these systems were assayed for toxicity to various species of Lepidoptera, Coleoptera, and Hemiptera. TIC2199 was assayed for toxicity to the Lepidopteran insect species Black cutworm (BCW, *Agrotis ipsilon*), Corn earworm (CEW, *Helicoverpa zea*, also known as Soybean podworm), Cabbage looper worm (CLW, *Trichoplusia ni*), European corn borer (ECB, *Ostrinia nubilalis*), Fall armyworm (FAW, *Spodoptera frugiperda*), Southern armyworm (SAW, *Spodoptera eridania*), Soybean looper (SBL, *Chrysodeixis includens*), Sugarcane borer (SCB, *Diatraea saccharalis*), Southwestern corn borer (SWC, *Diatraea grandiosella*), and Velvet bean caterpillar (VBC, *Anticarsia gemmatalis*); the Coleopteran species Western Corn Rootworm (WCR, *Diabrotica virgifera*) and Southern Corn Rootworm (SCR, *Diabrotica undecimpunctata howardii*); the Hemipteran species Tarnished plant bug (TPB, *Lygus lineolaris*), Western tarnished plant bug (*Lygus hesperus*), and Neotropical Brown Stink Bug (NBSB, *Euschistus heros*). The bioassay results are presented in Table 2 below wherein "+" indicates activity and "−" indicates no activity.

TABLE 2

Activity of TIC2199 against Lepidopteran, Coleopteran, and Hemipteran insect species.

| Lepidopteran | | | | | | | | | | | Coleopteran | | Hemipteran | | |
|---|---|---|---|---|---|---|---|---|---|---|---|---|---|---|---|
| BCW | CEW | CLW | ECB | FAW | SAW | SBL | SCB | SWC | VBC | WBC | WCR | SCR | TPB | WTP | NBSB |
| + | − | + | + | + | + | + | + | + | + | + | − | − | + | − | + |

As can be seen from the data presented in Table 2, TIC2199 demonstrated activity against the Lepidopteran species BCW, CLW, ECB, FAW, SAW, SBL, SCB, SWC, VBC, and WBC; and the Hemipteran species TPB and NBSB.

Example 3

Design of Artificial Coding Sequences for TIC2199 for Use in Expression in Plants Artificial coding sequences SEQ ID NOs:3, 6, 9, 12, 14, 16, and 18 encoding TIC2199 and truncations of TIC2199 were designed for expression in a plant cell. The artificial (alternatively referred to as synthetic) sequence was synthesized, according to methods generally described in U.S. Pat. No. 5,500,365, to avoid certain inimical problem sequences such as ATTTA and A/T rich plant polyadenylation sequences, while preserving the amino acid sequence of the native *Bacillus* protein.

The artificial sequences encoding TIC2199, TIC2199_1, TIC2199_2, and TIC2199_3 were cloned into plant transformation vectors and downstream of and functionally linked to plant promoters for driving expression of the coding sequence when in a plant cell, using skills known in the art. Five of the resulting transformation vectors used to transform corn plants comprised a first transgene cassette for expression of the TIC2199 pesticidal protein which comprised a constitutive promoter, operably linked 5' to a leader, operably linked 5' to an intron, operably linked 5' to an artificial coding sequence encoding TIC2199, which was in turn operably linked 5' to a 3' UTR and; a second transgene cassette for the selection of transformed plant cells using glyphosate selection. Nine plant transformation vectors also contained a chloroplast transit peptide (CTP) that was cloned operably linked 5' and in frame to the TIC2199 coding sequence to direct protein accumulation in the chloroplast. Six of the nine plant transformation vectors comprising a chloroplast transit peptide comprised the coding sequences SEQ ID NOs:3, 6, 9, or 12. Three of the nine plant transformation vectors comprising a chloroplast transit peptide comprised the coding sequences SEQ ID NOs:14, 16, or 18.

Example 4

TIC2199 Exhibits Lepidopteran Activity When Expressed in Stably Transformed Corn Plants Binary plant transformation vectors comprising transgene cassettes designed to express TIC2199 and TIC2199 truncation variant pesticidal proteins were cloned using methods known in the art. The resulting vectors were used to stably transform corn plants. Tissues were harvested from the transformants and used in insect bioassay against various Lepidopteran insect species.

Corn plants were transformed with the 6 binary transformation vectors as described in Example 3 using an *Agrobacterium*-mediated transformation method. The transformed cells were induced to form plants by methods known in the art. Bioassays using plant leaf disks were performed analogous to those described in U.S. Pat. No. 8,344,207. A single freshly hatched neonate larvae less than one day old was placed on each leaf disc sample and allowed to feed for approximately four days. A non-transformed corn plant was used to obtain tissue to be used as a negative control. Multiple transformation $R_0$ single-copy insertion events from each binary vector were assessed against Black cutworm (BCW, *Agrotis ipsilon*), European corn borer (ECB, *Ostrinia nubilalis*), Fall armyworm (FAW, *Spodoptera frugiperda*), and Southwestern corn borer (SWC, *Diatraea grandiosella*). An efficacy rating score which ranged from 0 to 3, 0 being no efficacy and 3 being highly efficacious, was assigned to each event based upon the percent leaf damage in the bioassay.

Based upon efficacy rating scores, TIC2199, TIC2199_1, TIC2199_2, and TIC2199_3 demonstrated an efficacy rating score of 3 in transformed $R_0$ single-copy events against ECB and SWC with or without a CTP and was highly efficacious against these two insect pest species.

Selected $R_0$ plants derived from 3 transformation vectors expressing TIC2199 were crossed with non-transformed wild-type elite variety plants to produce hybrid seed. Heterozygous $F_1$ seeds comprising TIC2199 were grown and assayed as described above against Black cutworm (BCW, *Agrotis ipsilon*), European corn borer (ECB, *Ostrinia nubilalis*), and Southwestern corn borer (SWC, *Diatraea grandiosella*). Based upon the efficacy rating scores, stably transformed heterozygous $F_1$ corn plants expressing TIC2199 were highly efficacious against ECB and SWC with or without a CTP.

Plants expressing TIC2199 were assayed against Sugarcane borer (SCB, *Diatraea saccharalis*) and Lesser cornstalk borer (LCSB, *Elasmopalpus lignosellus*) using leaf disc assays similar to those described above. TIC2199 was efficacious against SCB and highly efficacious against LCSB.

Example 5

Assay of Activity of TIC2199 Against Lepidopteran Insect Pests in Stably Transformed Soybean Plants Binary plant transformation vectors comprising transgene cassettes designed to express TIC2199 pesticidal protein is cloned using methods known in the art. The resulting vector is used to transform stably transformed soybean plants. Tissues are harvested from the transformants and used in insect bioassay against various Lepidopteran insect species.

The artificial coding sequence encoding TIC2199 and TIC2199 truncation variants is cloned into plant transformation vector constructs using skills known in the art. The resulting transformation vector constructs comprise a first transgene cassette for expression of the TIC2199 pesticidal protein which comprises a plant expressible promoter, operably linked 5' to a leader, optionally operably linked 5' to an intron, operably linked 5' to an artificial coding sequence encoding TIC2199, which is in turn operably linked 5' to a 3' UTR and; a second transgene cassette for the selection of transformed plant cells using spectinomycin selection. A chloroplast transit peptide (CTP) can optionally be cloned 5' and in-frame with the artificial TIC2199 coding sequence.

Soybean plants are transformed using an *Agrobacterium*-mediated transformation method. The transformed cells are induced to form plants by methods known in the art. Bioassays using plant leaf disks are performed analogous to those described in U.S. Pat. No. 8,344,207. A single freshly hatched neonate larvae less than one day old is placed on each leaf disc sample and allowed to feed for approximately four days. A non-transformed corn plant is used to obtain tissue to be used as a negative control. Multiple transformation $R_0$ single-copy insertion events from each binary vector are assessed against Lepidopteran insect species such as, but not limited to Black armyworm (BAW, *Spodoptera*

*cosmioides*), Southern armyworm (SAW, *Spodoptera eridania*), Soybean looper (SBL, *Chrysodeixis includens*), Soybean pod worm (SPW, *Helicoverpa zea*), Sunflower looper (SFL, *Rachiplusia nu*), and Velvet bean caterpillar (VBC, *Anticarsia gemmatalis*). An efficacy rating score which ranges from 0 to 3 is assigned to each event based upon the percent leaf damage in the bioassay for each event and the percent events that shared the lowest percent range of damage (Penetrance) as shown in Table 3.

TABLE 3

Efficacy rating scores.

| Efficacy score | Percent Leaf Damage | Penetrance |
|---|---|---|
| 0 | >50% | ≥80% |
| 1 | <50% | ≥20% |
| 2 | <30% | ≥20% |
| 3 | ≤10% | ≥50% |

Example 6

Assay of Activity of TIC2199 Against Hemipteran Insect Pests in Stably Transformed Soybean Plants Binary plant transformation vectors comprising transgene cassettes designed to express TIC2199 pesticidal protein is cloned using methods known in the art. The resulting vectors are used to transform stably transformed soybean plants. Tissues are harvested from the transformants and used in insect bioassay against various Lepidopteran insect species.

The artificial coding sequence encoding TIC2199 is cloned into plant transformation vector constructs using skills known in the art. The resulting transformation vector constructs are similar to those describe in Example 5 above. A chloroplast transit peptide (CTP) can optionally be cloned 5' and in-frame with the artificial TIC2199 coding sequence.

Soybean plants are transformed using an *Agrobacterium*-mediated transformation method. The transformed cells are induced to form plants by methods known in the art. Assay for activity against the Hemipteran pests is performed using a variety of techniques which will depend upon the species of Hemipteran pest and the preferred target tissue of that pest. For example, the Hemipteran pest species of Stink Bugs typically feed on the developing seeds and pods of the soybean plant. To assay for activity against Stink Bugs, R5 stage pods are harvested from the transgenic soybean plants expressing TIC2199 and placed in a covered Petri dish or large multi-well plate containing a layer of either agar or wet paper to provide humidity to the feeding environment. Second instar Stink Bug nymphs are placed in the Petri dish or large multi-well plate. A cover providing for the exchange of oxygen while preventing desiccation is placed over the feeding environment. The Stink Bug nymphs are allowed to feed for several days. Measurements of stunting and mortality are taken and compared to Stink Bugs nymphs feeding on pods from untransformed soybean plants.

Alternatively, assay of activity can also be performed on whole stably transformed plants. Transformed plants expressing TIC2199 are grown in a growth chamber or in the greenhouse. At R5 stage, the plants are enclosed in a cage made from breathable plastic "pollination" sheets (Vilutis and Company Inc, Frankfort, IL). The sheet sleeves are secured to the main stem just above the soil surface using a Velcro® tie. Each plant is infested with a specific number of second instar Stink Bug nymphs. The nymphs are released into each individual cage through a small slit on the cage side and then the cage is securely closed ensuring the insects won't escape. The nymphs are allowed to feed on the soybean pods for several days to a week or more. Observations are taken each day to determine measurements of stunting and mortality. At the end of the feeding period, the live and dead nymphs are collected. The plants are cut below the cages and moved to a laboratory where the insects are collected for each plant. Before opening the cage, the plants are vigorously shaken to ensure all of the insects fall off from their feeding sites to the base of the cage. Then the cage base is opened, and all plant material is removed and placed on a black sheet. The insects can be collected using an aspirator or some other means. The number of insects and their developmental stage is recorded for each plant. Also, the number and developmental stage of dead nymphs is also recorded. These measurements are compared to the measurements obtained from negative control, un-transformed plants.

Delays in development of the Stink Bug nymphs (stunting) or mortality are interpreted as an indication of toxicity if, when compared to the un-transformed controls, there is a significant difference.

Example 7

Assay of Activity of TIC2199 Against Hemipteran Insect Pests in Stably Transformed Cotton Plants This Example describes the assay of activity against Hemipteran insect pests in cotton plants stably transformed to express TIC2199.

Binary plant transformation vectors comprising transgene cassettes designed to express both plastid targeted and untargeted TIC2199 are cloned using methods known in the art.

Cotton plants are transformed using the binary plant transformation vectors. The transformed cotton plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs are typically seed feeders, and thus, injury to cotton bolls is the primary concern. They primarily damage cotton by piercing the bolls and feeding on the seeds. Their feeding activity can result in dark spots about 1/16 of an inch in diameter on the outside of larger bolls where feeding occurred. Seed feeding may result in reduced lint production and stained lint near the feeding site. Because of their size, adults and fourth and fifth instar nymphs have the greatest potential for damaging bolls, and it is therefore important to kill the insect in its earlier nymphal stages. The Hemipteran pest species of Lygus primarily feed on the squares and young bolls. The nymphs are more voracious feeders and tend to cause the most severe damage. When feeding on squares, Lygus target the developing anthers which often results in the square shriveling and falling from the plant. For those squares that develop into bolls, the bolls may have anthers that are incapable of forming pollen, unfertilized seeds, and empty locules. When feeding on bolls, Lygus target the developing seeds, causing small black sunken spots on the outside of the boll.

One method to assay activity of TIC2199 in stably transformed cotton plants is to use squares in an insect bioassay. The squares are harvested from transformed cotton plants expressing TIC2199. The squares can be put into a petri dish or each square into a well of a large well plate. Young neonate Lygus or Stink Bug nymphs are placed into the petri dish or large well plate and allowed to feed for a prescribed time. Measurements of stunting and mortality are taken over the time course of feeding and compared to controls in which squares derived from untransformed cotton plants are used in assay.

Alternatively, assay of activity can be performed on whole transformed cotton plants. For example, to assay against Lygus species, $R_1$ seeds derived from plants expressing one TIC2199 are sown in 10-inch pots. An untransformed cotton plant, preferably from the same variety as the transformed plants, is used as a negative control. Plants are maintained in an environment chamber with a photoperiod of sixteen (16) hours of light at thirty-two (32) degrees Celsius and eight (8) hours of dark at twenty-three (23) degrees Celsius, and a light intensity between eight hundred (800) and nine hundred (900) micro-Einsteins. At forty (40) to forty-five (45) days after planting, the individual plants are enclosed in a cage made from breathable plastic "pollination" sheets (Vilutis and Company Inc, Frankfort, IL). The sheet sleeves are secured to the main stem just above the soil surface using a Velcro® tie. Two pairs of sexually mature male and female *Lygus lineolaris* or *Lygus hesperus* adults (six days old) from a laboratory culture are collected into a fourteen-milliliter round-bottom plastic tube (Becton Dickinson Labware, Franklin Lakes, NJ) and used for each plant. The adults are released into each individual cage through a small slit on the cage side and then the cage is securely closed ensuring the insects would not escape. The insects are allowed to mate, and the plants are kept in the cage for twenty-one (21) days.

After twenty-one (21) days, the plants are then cut below the cages and moved to a laboratory where the insects are collected for each plant and counted. Before opening the cage, the plants are vigorously shaken to ensure all of the insects fall off from their feeding sites to the base of the cage. Then the cage base is opened and all plant material removed and placed on a black sheet. The insects are collected using an aspirator. The plant is then thoroughly inspected to recover any remaining insects. The number of insects collected and their developmental stage are recorded for each plant. The insect counts are divided into several groups based upon maturity of the Lygus: nymphs up to $3^{rd}$ instar, $4^{th}$ instar, $5^{th}$ instar and adults.

To assay against Stink Bug species, R1 seeds derived from plants expressing TIC2199 are sown into pots and grown and caged as described above. Untransformed cotton plants are also used as a negative control. Second instar Stink Bug nymphs are used to infest the plants and allowed to feed on the squares and bolls for several days or weeks. The caged plants are collected as described above and the collected stink bugs are examined and scored for mortality, as well as, maturity of the nymphs recorded. These scores are then compared to the negative control plants.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide segment encoding a pesticidal protein or pesticidal fragment thereof, wherein:

a) said pesticidal protein comprises the amino acid sequence of SEQ ID NOs: 10 or 15; or b) said pesticidal protein comprises an amino acid sequence having at least 98% amino acid sequence identity to SEQ ID NOs: 10 or 15.

2. A vector comprising the recombinant nucleic acid molecule of claim 1, wherein said vector is selected from the group consisting of a plasmid, phagemid, bacmid, cosmid, and a bacterial or yeast artificial chromosome.

3. A host cell comprising the recombinant nucleic acid molecule of claim 1, wherein said host cell is selected from the group consisting of a bacterial host cell and a plant cell.

4. The host cell of claim 3, wherein said bacterial host cell is from a genus of bacteria selected from the group consisting of: *Agrobacterium, Rhizobium, Bacillus, Brevibacillus, Escherichia, Pseudomonas, Klebsiella, Pantoea*, and *Erwinia*.

5. The host cell of claim 4, wherein said *Bacillus* is *Bacillus cereus* or *Bacillus thuringiensis*, said *Brevibacillus* is a *Brevibacillus laterosporus*, and said *Escherichia* is an *Escherichia coli*.

6. The host cell of claim 3, wherein said plant cell is a dicotyledonous or a monocotyledonous plant cell.

7. The host cell of claim 6, wherein said plant cell is selected from the group consisting of an alfalfa, banana, barley, bean, broccoli, cabbage, *brassica*, canola, carrot, cassava, castor, cauliflower, celery, chickpea, Chinese cabbage, citrus, coconut, coffee, corn, clover, cotton, cucurbit, cucumber, Douglas fir, eggplant, eucalyptus, flax, garlic, grape, hops, leek, lettuce, Loblolly pine, millet, melon, nut, oat, olive, onion, ornamental, palm, pasture grass, pea, peanut, pepper, pigeonpea, pine, potato, poplar, pumpkin, Radiata pine, radish, rapeseed, rice, rootstock, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plant cell.

8. The recombinant nucleic acid molecule of claim 1, wherein said protein exhibits activity against a Lepidopteran insect.

9. The recombinant nucleic acid molecule of claim 8, wherein said Lepidopteran insect is selected from the group consisting of: Black cutworm (*Agrotis ipsilon*), Corn earworm (*Helicoverpa zea*), Cabbage looper worm (*Trichoplusia ni*), European corn borer (*Ostrinia nubilalis*), Fall armyworm (*Spodoptera frugiperda*), Southern armyworm (*Spodoptera eridania*), Soybean looper (*Chrysodeixis includens*), Southwestern corn borer (*Diatraea grandiosella*), Sugarcane borer (*Diatraea* saccharalis), Velvet bean caterpillar (*Anticarsia gemmatalis*), Western bean cutworm (*Striacosta albicosta*), and Lesser cornstalk borer (*Elasmopalpus lignosellus*).

10. The recombinant nucleic acid molecule of claim 1, wherein said protein exhibits activity against a Hemipteran insect.

11. The recombinant nucleic acid molecule of claim 10, wherein said Hemipteran insect is selected from the group consisting of: Tarnished plant bug (*Lygus lineolaris*) and Neotropical brown stink bug (*Euschistus heros*).

12. A plant comprising the recombinant nucleic acid molecule of claim 1.

13. The plant of claim 12, wherein said plant is a monocot plant or a dicot plant.

14. The plant of claim 12, wherein the plant is selected from the group consisting of alfalfa, banana, barley, bean, broccoli, cabbage, brassica, canola, carrot, cassava, castor, cauliflower, celery, chickpea, Chinese cabbage, citrus, coconut, coffee, corn, clover, cotton, cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, corn, sweet gum, sweet potato, switchgrass, tea, tobacco, tomato, triticale, turf grass, watermelon, and wheat.

15. A seed producing the plant of claim 12, wherein said seed comprises said recombinant nucleic acid molecule.

16. An insect inhibitory composition comprising the recombinant nucleic acid molecule of claim 1.

17. The insect inhibitory composition of claim 16, further comprising a nucleotide sequence encoding at least one other pesticidal agent that is different from said pesticidal protein.

18. The insect inhibitory composition of claim 17, wherein said at least one other pesticidal agent is selected from the group consisting of an insect inhibitory protein, an insect inhibitory dsRNA molecule, a chemical molecule and an ancillary protein, wherein said at least one other pesticidal agent is toxic to the same pest as the pesticidal protein or pesticidal fragment thereof.

19. The insect inhibitory composition of claim 17, wherein said at least one other pesticidal agent exhibits activity against one or more pest species of the orders Lepidoptera, Coleoptera, or Hemiptera.

20. The insect inhibitory composition of claim 17, wherein said at least one other pesticidal protein is selected from the group consisting of Cry1A, Cry1Ab, Cry1Ac, Cry1A.105, Cry1Ae, Cry1B, Cry1C, Cry1C variants, Cry1D, Cry1D variants, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z, AXMI-225z, AXMI-238, AXMI-270, AXMI-279, AXMI-345, AXMI-335, AXMI-R1, AXMI-R1 variants, IP3, IP3 variants, DIG-3, DIG-5, DIG-10, DIG-657, DIG-11 protein, IDP102Aa, IDP102Aa homologs, IDP110Aa, IDP110Aa homologs TIC868, Cry1Da1_7, BCW003, TIC1100, TIC867, TIC867_23, TIC6757, TIC7641, IDP072Aa, TIC5290, TIC3668, TIC3669, TIC3670, IDP103, IDP103 homologs, PIP-50, PIP-65, PIP-65 homologs, PIP-83, PIP-83 homologs, and Cry1B.

21. The insect inhibitory composition of claim 16, defined as comprising a plant cell that expresses the pesticidal protein from the recombinant nucleic acid molecule.

22. A commodity product produced from the plant, or part thereof, of claim 12, wherein the commodity product comprises a detectable amount of said recombinant nucleic acid molecule.

23. The commodity product of claim 22, selected from the group consisting of commodity corn bagged by a grain handler, corn flakes, corn cakes, corn flour, corn meal, corn syrup, corn oil, corn silage, corn starch, corn cereal, soybean, rice, wheat, sorghum, pigeon pea, peanut, fruit, melon, juices, concentrates, jams, jellies, marmalades, whole cotton seed, processed cotton seed, cotton oil, lint, fiber, paper, biomasses, whole soybean seed, processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products.

24. A method of producing progeny seed comprising the recombinant nucleic acid molecule of claim 1, the method comprising:

a) planting a first seed comprising the recombinant nucleic acid molecule;

b) growing a plant from the seed of step a; and c) harvesting the progeny seed from the plant, wherein said harvested seed comprises said recombinant nucleic acid molecule.

25. A plant resistant to insect infestation, wherein the cells of said plant comprise the recombinant nucleic acid molecule of claim 1.

26. A method for controlling a Lepidopteran species pest or pest infestation, said method comprising contacting the pest with the recombinant nucleic acid molecule of claim 1 and the pesticidal protein it encodes.

27. A method for controlling a Lepidopteran pest species or pest infestation in a field, said method comprising:

a) growing a crop plant in a field, wherein said crop plant expresses an insecticidally effective amount of a pesticidal protein, wherein said pesticidal protein comprises the amino acid sequence of SEQ ID NOs 10 or 15 or an amino acid sequence having at least 98% amino acid sequence identity to SEQ ID NOs: 10 or 15; and b) releasing into said field transgenic Lepidopteran pest species carrying a self-limiting gene to reduce the likelihood of development of resistance of the pest species to the pesticidal protein.

28. The method of claim 27, wherein said crop plant is a monocotyledonous or dicotyledonous crop plant.

29. The method of claim 28, wherein the monocotyledonous crop plant is corn, wheat, sorghum, rice, rye, or millet.

30. The method of claim 29, wherein the monocotyledonous crop plant is corn.

31. The method of claim 27, wherein the dicotyledonous crop plant is soybean, cotton, or canola.

32. The recombinant nucleic acid molecule of claim 1, wherein said polynucleotide segment comprises the nucleotide sequence of SEQ ID NOs: 11, 12 or 16.

33. The recombinant nucleic acid molecule of claim 1, wherein said polynucleotide segment comprises a nucleotide sequence that is at least 95% identical to the nucleotide sequence of SEQ ID NOs: 11, 12 or 16.

* * * * *

SEQUENCE LISTING

```
Sequence total quantity: 18
SEQ ID NO: 1             moltype = DNA  length = 2160
FEATURE                  Location/Qualifiers
misc_feature             1..2160
                         note = Nucleic acid sequence encoding a TIC2199 pesticidal
                          protein obtained from Bacillus thuringiensis species
                          EG8639.
source                   1..2160
                         mol_type = unassigned DNA
                         organism = Bacillus thuringiensis
SEQUENCE: 1
atgaaaccaa agaatcaaaa tatgtatcaa agcttgtcta gcaatgtgac agttgataaa  60
atctctacaa atccactaaa aaatgaaaca gatatagaat tacaaaatat taatcatgaa  120
gcttgtttaa aaatgtctaa gtataaaaat gtagcgccat ttgttagcgc atcaacaatt  180
caaacgggga ttggaattgc tggtaagatt cttggtactc taggtgttcc ttttgctgga  240
caaatagcta gcctctatag ttttatctta ggcgagcttt ggcctaaagg gaaaagtcaa  300
tgggaaatct ttatggaaca tgtagaagag attattaatc aaaaaatatc aacttatgca  360
agaaataaag ctctttcaga cttgagagga ttaggggatg ctttagccgt ctaccatgaa  420
tcgcttgaaa gttgggttga aaatcgtaat aacactcgag cgaggagtgt agtcaagaac  480
caatatatcg cattagaact gatgtttgtt caaaaactac cttcttttgc agtatctggt  540
gaggaagtac cattattacc gatatacgcc caagctgcca atttacattt gttgttatta  600
agagatgtat ctatttttgg aaaagaatgg ggattatcag cttcagaaat ttcaacattt  660
tataaccgtc aagtcgaacg aacaagagat tattccgacc attgtgtaaa atggtataat  720
acaggcctaa ataacttgag gggtacaaat gccaaaagtt gggttcgtta taatcaattt  780
cgtaaagata tgacattaat ggtattagat ttagttgcgc tattcccaag ctatgataca  840
cttgtatatc ctattaaaac cacttcacaa cttacaagag aagtatatac agacgcaatt  900
gggaccgtgc atccgaatca agcttttgca agtacgactt ggtataataa taatgcacct  960
tcgttctctg ccatagaggc tgctgttatc cgaagtccac acctacttga ttttctagaa  1020
aaagttacaa tatacagctt attaagtcgg tggagtaata ctcagtatat gaatatgtgg  1080
ggaggacata gacttgaatc ccgcccaata ggaggggcat taaatacctc aacacaagga  1140
```

```
tctaccaata cttcgattaa tccagtaaca ttacagttca cgtctcgaga cgtttatagg  1200
actgaatcat gggcagggct gaatttattt ttaactcaac ctgttaatgg agtacctaga  1260
gttgatttcc attggaaatt cgtcacacat ccgatcgcat ctgataattt ctattatcca  1320
gggtatgctg gaattgggac acaattacaa gattcagaaa atgaattacc acctgaaaca  1380
acaggacagc caaattatga atcatatagt catagattat ctcatatagg actcatttca  1440
gcatcacatg tgaaagcatt ggtatattct tggacgcatc gtagtgcaga tcgtacaaat  1500
acaattgagc caaatagcat tacacaaata ccattagtaa aagcgttcaa tctttcttca  1560
ggtgccgctg ttgtgagagg accaggattt acaggtgggg atatccttcg aagaacgaat  1620
actggtacat ttggggatat acgagtaaat attaatccac catttgcaca aaggtatcgc  1680
gtaaggattc gctatgcttc tactacagat ttacaattcc atacgtcaat taacggtaaa  1740
gctattaatc aaggtaattt ttcagcaact atgaatagag gagaggactt agactataaa  1800
acctttagaa ctgtaggctt taccactcca tttagctttt cagatgtaca aagtacattc  1860
acaataggtg cttggaactt ctcttcaggt aacgaagttt atatagatag aattgaattt  1920
gttccggtag aagttacata tggggcagaa tatgattttg aaaaagcgca agagaaggtt  1980
actgcactgt ttacatctac gaatccaaga gaattaaaaa tagatgtaac ggattatcat  2040
attgaccagg tatcaaattt agtagagtct ctattagacg aattctatct tgatgaaaag  2100
agagaattat tcgagatagt taaatacgcg aagcaactct atattgagcg taacatgtag  2160

SEQ ID NO: 2            moltype = AA  length = 719
FEATURE                 Location/Qualifiers
REGION                  1..719
                        note = Amino acid sequence of the TIC2199 pesticidal
                         protein.
source                  1..719
                        mol_type = protein
                        organism = Bacillus thuringiensis
SEQUENCE: 2
MKPKNQNMYQ SLSSNVTVDK ISTNPLKNET DIELQNINHE ACLKMSKYKN VAPFVSASTI  60
QTGIGIAGKI LGTLGVPFAG QIASLYSFIL GELWPKGKSQ WEIFMEHVEE IINQKISTYA  120
RNKALSDLRG LGDALAVYHE SLESWVENRN NTRARSVVKN QYIALELMFV QKLPSFAVSG  180
EEVPLLPIYA QAANLHLLLL RDVSIFGKEW GLSASEISTF YNRQVERTRD YSDHCVKWYN  240
TGLNNLRGTN AKSWVRYNQF RKDMTLMVLD LVALFPSYDT LVYPIKTTSQ LTREVYTDAI  300
GTVHPNQAFA STTWYNNNAP SFSAIEAAVI RSPHLLDFLE KVTIYSLLSR WSNTQYMNMW  360
GGHRLESRPI GGALNTSTQG STNTSINPVT LQFTSRDVYR TESWAGLNLF LTQPVNGVPR  420
VDFHWKFVTH PIASDNFYYP GYAGIGTQLQ DSENELPPET TGQPNYESYS HRLSHIGLIS  480
ASHVKALVYS WTHRSADRTN TIEPNSITQI PLVKAFNLSS GAAVVRGPGF TGGDILRRTN  540
TGTFGDIRVN INPPFAQRYR VRIRYASTTD LQFHTSINGK AINQGNFSAT MNRGEDLDYK  600
TFRTVGFTTP FSFSDVQSTF TIGAWNFSSG NEVYIDRIEF VPVEVTYGAE YDFEKAQEKV  660
TALFTSTNPR ELKIDVTDYH IDQVSNLVES LLDEFYLDEK RELFEIVKYA KQLYIERNM   719

SEQ ID NO: 3            moltype = DNA  length = 2160
FEATURE                 Location/Qualifiers
misc_feature            1..2160
                        note = Synthetic coding sequence used for expression in a
                         plant cell encoding TIC2199.
source                  1..2160
                        mol_type = other DNA
                        organism = synthetic construct
SEQUENCE: 3
atgaagccca agaatcagaa catgtaccag tccctcagct cgaacgtcac cgtcgataag  60
attagcacca acccgctcaa gaatgagacc gacatcgaat tacagaacat taaccacgag  120
gcgtgcctca agatgtctaa gtacaagaac gtcgcaccct tcgtctcggc ttctacgatc  180
cagacgggca ttggcatcgc cgggaagata ctcggcacac tcggcgtccc gttcgctggt  240
caaatcgcct cgctctactc cttcatactc ggtgaactgt ggccgaaggg caagtcgcag  300
tgggaaatct tcatggagca cgtggaggag atcatcaacc agaagataag cacctacgcc  360
cgtaacaagg cgctgagcga cctccgtggg ctgggcgatg cgctggcggt gtaccacgag  420
tcgctggagt cgtgggtgga gaaccgcaac aacacccgcg cccggtccgt ggtcaagaac  480
cagtacattg ccctggagct gatgttcgtg cagaagctcc cgtccttcgc ggtgtccggc  540
gaggaagtgc cactgttgcc catctacgcc caagcagcca acctgcacct ccttctcctc  600
cgggacgtca gcatcttcgg gaaggagtgg ggcctttcag cgtcagagat ttcaaccttc  660
tacaacaggc aagttgagcg cacgcgcgac tactcggacc actgcgtcaa gtggtacaac  720
accggcctca acaacctgcg tggaacgaac gccaagagct gggtccgcta caaccagttt  780
cgaaaggaca tgaccctcat ggtgctggac cttgtggcct tgttcccgtc ctacgacacc  840
ctcgtttatc cgattaagac tacatctcaa cttacccgcg aggtttacac agacgccata  900
gggaccgtgc atcctaacca ggcgttcgca tcgacaactt ggtacaacaa caacgcgccc  960
tcgttctcag ccatcgaggc cgccgtgatc cgttcaccgc acctcctgga cttcctggag  1020
aaggttacca tctactccct cttgtctcgc tggagtaata ctcagtacat gaacatgtgg  1080
ggaggacatc gcctcgaatc tcgaccgatt ggcggcgcgc ttaacacatc cacacagggc  1140
tccacgaaca ccagcatcaa cccggtgacg ttgcaattca cttcacgcga tgtctatcgg  1200
accgagagct gggctggcct gaacctgttc ctaactcagc ccgtgaacgg tgtgcccaga  1260
gtcgatttcc actggaaatt cgtcactcat cccatcgcca gcgacaactt ctactaccca  1320
ggctacgccg gtatcggcac acagcttcaa gactccgaga acgaactgcc tcccgagact  1380
actggccagc cgaactacga gagttactcc cataggcttt cgcacatcgg cctaatctca  1440
gcttcgcatg ttaaagcact cgtgtactca tggacacaca gaagcgccga cagaacgaac  1500
accattgagc caaactctat cacgcagatc ccgctggtta aggcgttcaa cttgtcgagc  1560
ggcgctgcgg tcgtgcgcgg acctggattc accggtggcg acattctgcg ccgcaccaac  1620
acaggaacct tcggcgacat ccgggtgaac atcaacccgc cgtttgcaca acgctatcgc  1680
gtcaggatac ggtacgcatc cacgacggac ctccagttcc acaccagcat caacgggaag  1740
gctatcaacc agggaaactt tagcgccacg atgaaccgtg gtgaggactt ggactacaag  1800
```

-continued

```
acattccgga cggtcggctt cacgacgccc ttcagcttta gcgacgtcca gtccaccttc  1860
accatcggag catggaactt cagtagcggc aacgaggtgt acatcgaccg aatcgagttc  1920
gtcccggttg aggtgaccta cggagccgaa tacgacttcg agaaggcaca ggagaaggtg  1980
actgctctgt ttacaagcac aaatcctcgg gaactaaaga tcgacgtcac agactaccac  2040
atcgaccaag ttagcaacct cgtcgagagc ctcctggacg agttctattt ggacgagaag  2100
cgggagctgt tcgagatcgt gaaatacgcc aagcagttgt acatcgagcg taacatgtga  2160

SEQ ID NO: 4            moltype = AA  length = 611
FEATURE                 Location/Qualifiers
REGION                  1..611
                        note = An amino acid sequence of a fragment of TIC2199
                         wherein the N-terminal signal peptide and protoxin domain
                         has been removed.
source                  1..611
                        mol_type = protein
                        organism = Bacillus thuringiensis
SEQUENCE: 4
MSKYKNVAPF VSASTIQTGI GIAGKILGTL GVPFAGQIAS LYSFILGELW PKGKSQWEIF  60
MEHVEEIINQ KISTYARNKA LSDLRGLGDA LAVYHESLES WVENRNNTRA RSVVKNQYIA  120
LELMFVQKLP SFAVSGEEVP LLPIYAQAAN LHLLLLRDVS IFGKEWGLSA SEISTFYNRQ  180
VERTRDYSDH CVKWYNTGLN NLRGTNAKSW VRYNQFRKDM TLMVLDLVAL FPSYDTLVYP  240
IKTTSQLTRE VYTDAIGTVH PNQAFASTTW YNNNAPSFSA IEAAVIRSPH LLDFLEKVTI  300
YSLLSRWSNT QYMNMWGGHR LESRPIGGAL NTSTQGSTNT SINPVTLQFT SRDVYRTESW  360
AGLNLFLTQP VNGVPRVDFH WKFVTHPIAS DNFYYPGYAG IGTQLQDSEN ELPPETTGQP  420
NYESYSHRLS HIGLISASHV KALVYSWTHR SADRTNTIEP NSITQIPLVK AFNLSSGAAV  480
VRGPGFTGGD ILRRTNTGTF GDIRVNINPP FAQRYRVRIR YASTTDLQFH TSINGKAINQ  540
GNFSATMNRG EDLDYKTFRT VGFTTPFSFS DVQSTFTIGA WNFSSGNEVY IDRIEFVPVE  600
VTYGAEYDFE K                                                      611

SEQ ID NO: 5            moltype = DNA  length = 1836
FEATURE                 Location/Qualifiers
misc_feature            1..1836
                        note = A DNA sequence encoding the truncated TIC2199
                         protein of SEQ ID NO:4 for expression in bacteria.
source                  1..1836
                        mol_type = other DNA
                        organism = synthetic construct
SEQUENCE: 5
atgtctaagt ataaaaatgt agcgccattt gttagcgcat caacaattca aacggggatt  60
ggaattgctg gtaagattct tggtactcta ggtgttcctt ttgctggaca aatagctagc  120
ctctatagtt ttatcttagg cgagctttgg cctaaaggga aaagtcaatg ggaaatcttt  180
atggaacatg tagaagagat tattaatcaa aaaatatcaa cttatgcaag aaataaagct  240
ctttcagact tgagaggatt aggggatgct ttagccgtct accatgaatc gcttgaaagt  300
tgggttgaaa atcgtaataa cactcgagcg aggagtgtag tcaagaacca atatatcgca  360
ttagaactga tgtttgttca aaaactacct tcttttgcag tatctggtga ggaagtacca  420
ttattaccga tatacgccca agctgccaat ttacatttgt tgttattaag agatgtatct  480
atttttggaa aagaatgggg attatcagct tcagaaattt caacatttta taaccgtcaa  540
gtcgaacgaa caagagatta ttccgaccat tgtgtaaaat ggtataatac aggcctaaat  600
aacttgaggg gtacaaatgc caaaagttgg gttcgttata atcaatttcg taaagatatg  660
acattaatgg tattagattt agttgcgcta ttcccaagct atgatacact tgtatatcct  720
attaaaacca cttcacaact tacaagagaa gtatatacag acgcaattgg gaccgtgcat  780
ccgaatcaag cttttgcaag tacgacttgg tataataata atgcaccttc gttctctgcc  840
atagaggctg ctgttatccg aagtccacac ctacttgatt ttctagaaaa agttacaata  900
tacagcttat taagtcggtg gagtaatact cagtatatga atatgtgggg aggacataga  960
cttgaatccc gcccaatagg aggggcatta aatacctcaa cacaaggatc taccaatact  1020
tcgattaatc cagtaacatt acagttcacg tctcgagacg tttataggac tgaatcatgg  1080
gcagggctga atttattttt aactcaacct gttaatggag tacctagagt tgatttccat  1140
tggaaattcg tcacacatcc gatcgcatct gataatttct attatccagg gtatgctgga  1200
attgggacac aattacaaga ttcagaaaat gaattaccac ctgaaacaac aggacagcca  1260
aattatgaat catatagtca tagattatct catataggac tcatttcagc atcacatgtg  1320
aaagcattgg tatattcttg gacgcatcgt agtgcagatc gtacaaatac aattgagcca  1380
aatagcatta cacaaatacc attagtaaaa gcgttcaatc tttcttcagg tgccgctgtt  1440
gtgagaggac caggatttac aggtggggat atccttcgaa gaacgaatac tggtacattt  1500
ggggatatac gagtaaatat taatccacca tttgcacaaa ggtatcgcgt aaggattcgc  1560
tatgcttcta ctacagattt acaattccat acgtcaatta acggtaaagc tattaatcaa  1620
ggtaattttt cagcaactat gaatagagga gaggacttag actataaaac ctttagaact  1680
gtaggcttta ccactccatt tagcttttca gatgtacaaa gtacattcac aataggtgct  1740
tggaacttct cttcaggtaa cgaagtttat atagatagaa ttgaatttgt tccggtagaa  1800
gttacatatg gggcagaata tgattttgaa aaatag                            1836

SEQ ID NO: 6            moltype = DNA  length = 1836
FEATURE                 Location/Qualifiers
misc_feature            1..1836
                        note = A synthetic coding sequence encoding the truncated
                         TIC2199 of SEQ ID NO:4 and capable of use in a plant cell.
source                  1..1836
                        mol_type = other DNA
                        organism = synthetic construct
```

-continued

```
SEQUENCE: 6
atgtctaagt acaagaacgt cgcacccttc gtctcggctt ctacgatcca gacgggcatt  60
ggcatcgccg ggaagatact cggcacactc ggcgtcccgt tcgctggtca aatcgcctcg  120
ctctactcct tcatactcgg tgaactgtgg ccgaagggca agtcgcagtg ggaaatcttc  180
atggagcacg tggaggagat catcaaccag aagataagca cctacgcccg taacaaggcg  240
ctgagcgacc tccgtgggct gggcgatgcg ctggcggtgt accacgagtc gctggagtcg  300
tgggtggaga accgcaacaa cacccgcgcc cggtccgtgg tcaagaacca gtacattgcc  360
ctggagctga tgttcgtgca gaagctcccg tccttcgcgg tgtccggcga ggaagtgcca  420
ctgttgccca tctacgccca agcagccaac ctgcacctcc ttctcctccg ggacgtcagc  480
atcttcggga aggagtgggg cctttcagcg tcagagattt caaccttcta caacaggcaa  540
gttgagcgca cgcgcgacta ctcggaccac tgcgtcaagt ggtacaacac cggcctcaac  600
aacctgcgtg gaacgaacgc caagagctgg gtccgctaca accagtttcg aaaggacatg  660
accctcatgg tgctggacct tgtggccttg ttcccgtcct acgacaccct cgtttatccg  720
attaagacta catctcaact tacccgcgag gtttacacag acgccatagg gaccgtgcat  780
cctaaccagg cgttcgcatc gacaacttgg tacaacaaca acgcgccctc gttctcagcc  840
atcgaggccg ccgtgatccg ttcaccgcac ctcctggact tcctggagaa ggttaccatc  900
tactccctct tgtctcgctg gagtaatact cagtacatga acatgtgggg aggacatcgc  960
ctcgaatctc gaccgattgg cggcgcgctt aacacatcca cacagggctc cacgaacacc  1020
agcatcaacc cggtgacgtt gcaattcact tcacgcgatg tctatcggac cgagagctgg  1080
gctggcctga acctgttcct aactcagccc gtgaacggtg tgcccagagt cgatttccac  1140
tggaaattcg tcactcatcc catcgccagc gacaacttct actacccagg ctacgccggt  1200
atcggcacac agcttcaaga ctccgagaac gaactgcctc ccgagactac tggccagccg  1260
aactacgaga gttactccca taggctttcg cacatcggcc taatctcagc ttcgcatgtt  1320
aaagcactcg tgtactcatg gacacacaga agcgccgaca gaacgaacac cattgagcca  1380
aactctatca cgcagatccc gctggttaag gcgttcaact tgtcgagcgg cgctgcggtc  1440
gtgcgcggac ctggattcac cggtggcgac attctgcgcc gcaccaacac aggaaccttc  1500
ggcgacatcc gggtgaacat caacccgccg tttgcacaac gctatcgcgt caggatacgg  1560
tacgcatcca cgacggacct ccagttccac accagcatca acgggaaggc tatcaaccag  1620
ggaaacttta gcgccacgat gaaccgtggt gaggacttgg actacaagac attccggacg  1680
gtcggcttca cgacgccctt cagctttagc gacgtccagt ccaccttcac catcggagca  1740
tggaacttca gtagcggcaa cgaggtgtac atcgaccgaa tcgagttcgt cccggttgag  1800
gtgacctacg gagccgaata cgacttcgag aagtga                           1836

SEQ ID NO: 7            moltype = AA  length = 675
FEATURE                 Location/Qualifiers
REGION                  1..675
                        note = An amino acid sequence of a variant of TIC2199,
                         TIC2199_1 in which the N-terminal 44 amino acids
                         comprising a secretion peptide have been removed.
source                  1..675
                        mol_type = protein
                        organism = synthetic construct
SEQUENCE: 7
MSKYKNVAPF VSASTIQTGI GIAGKILGTL GVPFAGQIAS LYSFILGELW PKGKSQWEIF  60
MEHVEEIINQ KISTYARNKA LSDLRGLGDA LAVYHESLES WVENRNNTRA RSVVKNQYIA  120
LELMFVQKLP SFAVSGEEVP LLPIYAQAAN LHLLLLRDVS IFGKEWGLSA SEISTFYNRQ  180
VERTRDYSDH CVKWYNTGLN NLRGTNAKSW VRYNQFRKDM TLMVLDLVAL FPSYDTLVYP  240
IKTTSQLTRE VYTDAIGTVH PNQAFASTTW YNNNAPSFSA IEAAVIRSPH LLDFLEKVTI  300
YSLLSRWSNT QYMNMWGGHR LESRPIGGAL NTSTQGSTNT SINPVTLQFT SRDVYRTESW  360
AGLNLFLTQP VNGVPRVDFH WKFVTHPIAS DNFYYPGYAG IGTQLQDSEN ELPPETTGQP  420
NYESYSHRLS HIGLISASHV KALVYSWTHR SADRTNTIEP NSITQIPLVK AFNLSSGAAV  480
VRGPGFTGGD ILRRTNTGTF GDIRVNINPP FAQRYRVRIR YASTTDLQFH TSINGKAINQ  540
GNFSATMNRG EDLDYKTFRT VGFTTPFSFS DVQSTFTIGA WNFSSGNEVY IDRIEFVPVE  600
VTYGAEYDFE KAQEKVTALF TSTNPRELKI DVTDYHIDQV SNLVESLLDE FYLDEKRELF  660
EIVKYAKQLY IERNM                                                  675

SEQ ID NO: 8            moltype = DNA  length = 2028
FEATURE                 Location/Qualifiers
misc_feature            1..2028
                        note = A DNA sequence encoding the TIC2199_1 variant of SEQ
                         ID NO:7.
source                  1..2028
                        mol_type = other DNA
                        organism = synthetic construct
SEQUENCE: 8
atgtctaagt ataaaaatgt agcgccattt gttagcgcat caacaattca aacggggatt  60
ggaattgctg gtaagattct tggtactcta ggtgttcctt ttgctggaca aatagctagc  120
ctctatagtt ttatcttagg cgagctttgg cctaaaggga aaagtcaatg ggaaatcttt  180
atggaacatg tagaagagat tattaatcaa aaaatatcaa cttatgcaag aaataaagct  240
ctttcagact tgagaggatt aggggatgct ttagccgtct accatgaatc gcttgaaagt  300
tgggttgaaa atcgtaataa cactcgagcg aggagtgtag tcaagaacca atatatcgca  360
ttagaactga tgtttgttca aaaactacct tcttttgcag tatctggtga ggaagtacca  420
ttattaccga tatacgccca agctgccaat ttacatttgt tgttattaag agatgtatct  480
atttttggaa aagaatgggg attatcagct tcagaaattt caacatttta taaccgtcaa  540
gtcgaacgaa caagagatta ttccgaccat tgtgtaaaat ggtataatac aggcctaaat  600
aacttgaggg gtacaaatgc caaaagttgg gttcgttata atcaatttcg taaagatatg  660
acattaatgg tattagattt agttgcgcta ttcccaagct atgatacact tgtatatcct  720
attaaaacca cttcacaact tacaagagaa gtatatacag acgcaattgg gaccgtgcat  780
ccgaatcaag cttttgcaag tacgacttgg tataataata atgcaccttc gttctctgcc  840
```

```
atagaggctg ctgttatccg aagtccacac ctacttgatt ttctagaaaa agttacaata  900
tacagcttat taagtcggtg gagtaatact cagtatatga atatgtgggg aggacataga  960
cttgaatccc gcccaatagg aggggcatta aatacctcaa cacaaggatc taccaatact  1020
tcgattaatc cagtaacatt acagttcacg tctcgagacg tttataggac tgaatcatgg  1080
gcagggctga atttattttt aactcaacct gttaatggag tacctagagt tgatttccat  1140
tggaaattcg tcacacatcc gatcgcatct gataatttct attatccagg gtatgctgga  1200
attgggacac aattacaaga ttcagaaaat gaattaccac ctgaaacaac aggacagcca  1260
aattatgaat catatagtca tagattatct catataggac tcatttcagc atcacatgtg  1320
aaagcattgg tatattcttg gacgcatcgt agtgcagatc gtacaaatac aattgagcca  1380
aatagcatta cacaaatacc attagtaaaa gcgttcaatc tttcttcagg tgccgctgtt  1440
gtgagaggac caggatttac aggtggggat atccttcgaa gaacgaatac tggtacattt  1500
ggggatatac gagtaaatat taatccacca tttgcacaaa ggtatcgcgt aaggattcgc  1560
tatgcttcta ctacagattt acaattccat acgtcaatta acggtaaagc tattaatcaa  1620
ggtaattttt cagcaactat gaatagagga gaggacttag actataaaac ctttagaact  1680
gtaggcttta ccactccatt tagcttttca gatgtacaaa gtacattcac aataggtgct  1740
tggaacttct cttcaggtaa cgaagtttat atagatagaa ttgaatttgt tccggtagaa  1800
gttacatatg gggcagaata tgattttgaa aaagcgcaag agaaggttac tgcactgttt  1860
acatctacga atccaagaga attaaaaata gatgtaacgg attatcatat tgaccaggta  1920
tcaaatttag tagagtctct attagacgaa ttctatcttg atgaaaagag agaattattc  1980
gagatagtta aatacgcgaa gcaactctat attgagcgta acatgtag              2028
```

```
SEQ ID NO: 9            moltype = DNA  length = 2028
FEATURE                 Location/Qualifiers
misc_feature            1..2028
                        note = A synthetic coding sequence encoding the TIC2199_1
                         variant of SEQ ID NO:7 and capable of use in a plant cell.
source                  1..2028
                        mol_type = other DNA
                        organism = synthetic construct
SEQUENCE: 9
atgtctaagt acaagaacgt cgcacccttc gtctcggctt ctacgatcca gacgggcatt  60
ggcatcgccg ggaagatact cggcacactc ggcgtcccgt tcgctggtca aatcgcctcg  120
ctctactcct tcatactcgg tgaactgtgg ccgaagggca agtcgcagtg ggaaatcttc  180
atggagcacg tggaggagat catcaaccag aagataagca cctacgcccg taacaaggcg  240
ctgagcgacc tccgtgggct gggcgatgcg ctggcggtgt accacgagtc gctggagtcg  300
tgggtggaga accgcaacaa cacccgcgcc cggtccgtgg tcaagaacca gtacattgcc  360
ctggagctga tgttcgtgca gaagctcccg tccttcgcgg tgtccggcga ggaagtgcca  420
ctgttgccca tctacgccca agcagccaac ctgcacctcc ttctcctccg ggacgtcagc  480
atcttcggga aggagtgggg cctttcagcg tcagagattt caaccttcta caacaggcaa  540
gttgagcgca cgcgcgacta ctcggaccac tgcgtcaagt ggtacaacac cggcctcaac  600
aacctgcgtg gaacgaacgc caagagctgg gtccgctaca accagtttcg aaaggacatg  660
accctcatgg tgctggacct tgtggccttg ttcccgtcct acgacaccct cgtttatccg  720
attaagacta catctcaact tacccgcgag gtttacacag acgccatagg gaccgtgcat  780
cctaaccagg cgttcgcatc gacaacttgg tacaacaaca acgcgccctc gttctcagcc  840
atcgaggccg ccgtgatccg ttcaccgcac ctcctggact tcctggagaa ggttaccatc  900
tactccctct tgtctcgctg gagtaatact cagtacatga acatgtgggg aggacatcgc  960
ctcgaatctc gaccgattgg cggcgcgctt aacacatcca cacagggctc cacgaacacc  1020
agcatcaacc cggtgacgtt gcaattcact tcacgcgatg tctatcggac cgagagctgg  1080
gctggcctga acctgttcct aactcagccc gtgaacggtg tgcccagagt cgatttccac  1140
tggaaattcg tcactcatcc catcgccagc gacaacttct actacccagg ctacgccggt  1200
atcggcacac agcttcaaga ctccgagaac gaactgcctc ccgagactac tggccagccg  1260
aactacgaga gttactccca taggctttcg cacatcggcc taatctcagc ttcgcatgtt  1320
aaagcactcg tgtactcatg gacacacaga agcgccgaca gaacgaacac cattgagcca  1380
aactctatca cgcagatccc gctggttaag gcgttcaact tgtcgagcgg cgctgcggtc  1440
gtgcgcggac ctggattcac cggtggcgac attctgcgcc gcaccaacac aggaaccttc  1500
ggcgacatcc gggtgaacat caacccgccg tttgcacaac gctatcgcgt caggatacgg  1560
tacgcatcca cgacggacct ccagttccac accagcatca acgggaaggc tatcaaccag  1620
ggaaacttta gcgccacgat gaaccgtggt gaggacttgg actacaagac attccggacg  1680
gtcggcttca cgacgccctt cagctttagc gacgtccagt ccaccttcac catcggagca  1740
tggaacttca gtagcggcaa cgaggtgtac atcgaccgaa tcgagttcgt cccggttgag  1800
gtgacctacg gagccgaata cgacttcgag aaggcacagg agaaggtgac tgctctgttt  1860
acaagcacaa atcctcggga actaaagatc gacgtcacag actaccacat cgaccaagtt  1920
agcaacctcg tcgagagcct cctggacgag ttctatttgg acgagaagcg ggagctgttc  1980
gagatcgtga aatacgccaa gcagttgtac atcgagcgta acatgtga              2028
```

```
SEQ ID NO: 10           moltype = AA  length = 655
FEATURE                 Location/Qualifiers
REGION                  1..655
                        note = An amino acid sequence of a variant of TIC2199,
                         TIC2199_2 in which the C-terminal 64 amino acids are also
                         removed.
source                  1..655
                        mol_type = protein
                        organism = synthetic construct
SEQUENCE: 10
MKPKNQNMYQ SLSSNVTVDK ISTNPLKNET DIELQNINHE ACLKMSKYKN VAPFVSASTI  60
QTGIGIAGKI LGTLGVPFAG QIASLYSFIL GELWPKGKSQ WEIFMEHVEE IINQKISTYA  120
RNKALSDLRG LGDALAVYHE SLESWVENRN NTRARSVVKN QYIALELMFV QKLPSFAVSG  180
EEVPLLPIYA QAANLHLLLL RDVSIFGKEW GLSASEISTF YNRQVERTRD YSDHCVKWYN  240
```

-continued

```
TGLNNLRGTN AKSWVRYNQF RKDMTLMVLD LVALFPSYDT LVYPIKTTSQ LTREVYTDAI  300
GTVHPNQAFA STTWYNNNAP SFSAIEAAVI RSPHLLDFLE KVTIYSLLSR WSNTQYMNMW  360
GGHRLESRPI GGALNTSTQG STNTSINPVT LQFTSRDVYR TESWAGLNLF LTQPVNGVPR  420
VDFHWKFVTH PIASDNFYYP GYAGIGTQLQ DSENELPPET TGQPNYESYS HRLSHIGLIS  480
ASHVKALVYS WTHRSADRTN TIEPNSITQI PLVKAFNLSS GAAVVRGPGF TGGDILRRTN  540
TGTFGDIRVN INPPFAQRYR VRIRYASTTD LQFHTSINGK AINQGNFSAT MNRGEDLDYK  600
TFRTVGFTTP FSFSDVQSTF TIGAWNFSSG NEVYIDRIEF VPVEVTYGAE YDFEK       655

SEQ ID NO: 11           moltype = DNA  length = 1968
FEATURE                 Location/Qualifiers
misc_feature            1..1968
                        note = A DNA sequence encoding the TIC2199_2 variant of SEQ
                         ID NO:10.
source                  1..1968
                        mol_type = other DNA
                        organism = synthetic construct
SEQUENCE: 11
atgaaaccaa agaatcaaaa tatgtatcaa agcttgtcta gcaatgtgac agttgataaa  60
atctctacaa atccactaaa aaatgaaaca gatatagaat tacaaaatat taatcatgaa  120
gcttgtttaa aaatgtctaa gtataaaaat gtagcgccat ttgttagcgc atcaacaatt  180
caaacgggga ttggaattgc tggtaagatt cttggtactc taggtgttcc ttttgctgga  240
caaatagcta gcctctatag ttttatctta ggcgagcttt ggcctaaagg gaaaagtcaa  300
tgggaaatct ttatggaaca tgtagaagag attattaatc aaaaaatatc aacttatgca  360
agaaataaag ctctttcaga cttgagagga ttaggggatg ctttagccgt ctaccatgaa  420
tcgcttgaaa gttgggttga aaatcgtaat aacactcgag cgaggagtgt agtcaagaac  480
caatatatcg cattagaact gatgtttgtt caaaaactac cttcttttgc agtatctggt  540
gaggaagtac cattattacc gatatacgcc caagctgcca atttacattt gttgttatta  600
agagatgtat ctatttttgg aaaagaatgg ggattatcag cttcagaaat ttcaacattt  660
tataaccgtc aagtcgaacg aacaagagat tattccgacc attgtgtaaa atggtataat  720
acaggcctaa ataacttgag gggtacaaat gccaaaagtt gggttcgtta taatcaattt  780
cgtaaagata tgacattaat ggtattagat ttagttgcgc tattcccaag ctatgataca  840
cttgtatatc ctattaaaac cacttcacaa cttacaagag aagtatatac agacgcaatt  900
gggaccgtgc atccgaatca agcttttgca agtacgactt ggtataataa taatgcacct  960
tcgttctctg ccatagaggc tgctgttatc cgaagtccac acctacttga ttttctagaa  1020
aaagttacaa tatacagctt attaagtcgg tggagtaata ctcagtatat gaatatgtgg  1080
ggaggacata gacttgaatc ccgcccaata ggaggggcat taaatacctc aacacaagga  1140
tctaccaata cttcgattaa tccagtaaca ttacagttca cgtctcgaga cgtttatagg  1200
actgaatcat gggcagggct gaatttattt ttaactcaac ctgttaatgg agtacctaga  1260
gttgatttcc attggaaatt cgtcacacat ccgatcgcat ctgataattt ctattatcca  1320
gggtatgctg gaattgggac acaattacaa gattcagaaa atgaattacc acctgaaaca  1380
acaggacagc caaattatga atcatatagt catagattat ctcatatagg actcatttca  1440
gcatcacatg tgaaagcatt ggtatattct tggacgcatc gtagtgcaga tcgtacaaat  1500
acaattgagc caaatagcat tacacaaata ccattagtaa aagcgttcaa tctttcttca  1560
ggtgccgctg ttgtgagagg accaggattt acaggtgggg atatccttcg aagaacgaat  1620
actggtacat ttggggatat acgagtaaat attaatccac catttgcaca aaggtatcgc  1680
gtaaggattc gctatgcttc tactacagat ttacaattcc atacgtcaat taacggtaaa  1740
gctattaatc aaggtaattt ttcagcaact atgaatagag gagaggactt agactataaa  1800
acctttagaa ctgtaggctt taccactcca tttagctttt cagatgtaca aagtacattc  1860
acaataggtg cttggaactt ctcttcaggt aacgaagttt atatagatag aattgaattt  1920
gttccggtag aagttacata tggggcagaa tatgattttg aaaaatga              1968

SEQ ID NO: 12           moltype = DNA  length = 1968
FEATURE                 Location/Qualifiers
misc_feature            1..1968
                        note = A synthetic coding sequence encoding the TIC2199_2
                         variant of SEQ ID NO:10 and capable of use in a plant cell.
source                  1..1968
                        mol_type = other DNA
                        organism = synthetic construct
SEQUENCE: 12
atgaagccca agaatcagaa catgtaccag tccctcagct cgaacgtcac cgtcgataag  60
attagcacca acccgctcaa gaatgagacc gacatcgaat tacagaacat taaccacgag  120
gcgtgcctca agatgtctaa gtacaagaac gtcgcaccct tcgtctcggc ttctacgatc  180
cagacgggca ttggcatcgc cgggaagata ctcggcacac tcggcgtccc gttcgctggt  240
caaatcgcct cgctctactc cttcatactc ggtgaactgt ggccgaaggg caagtcgcag  300
tgggaaatct tcatggagca cgtggaggag atcatcaacc agaagataag cacctacgcc  360
cgtaacaagg cgctgagcga cctccgtggg ctgggcgatg cgctggcggt gtaccacgag  420
tcgctggagt cgtgggtgga gaaccgcaac aacacccgcg cccggtccgt ggtcaagaac  480
cagtacattg ccctggagct gatgttcgtg cagaagctcc cgtccttcgc ggtgtccggc  540
gaggaagtgc cactgttgcc catctacgcc caagcagcca acctgcacct ccttctcctc  600
cgggacgtca gcatcttcgg gaaggagtgg ggcctttcag cgtcagagat ttcaaccttc  660
tacaacaggc aagttgagcg cacgcgcgac tactcggacc actgcgtcaa gtggtacaac  720
accggcctca acaacctgcg tggaacgaac gccaagagct gggtccgcta caaccagttt  780
cgaaaggaca tgaccctcat ggtgctggac cttgtggcct tgttcccgtc ctacgacacc  840
ctcgtttatc cgattaagac tacatctcaa cttacccgcg aggtttacac agacgccata  900
gggaccgtgc atcctaacca ggcgttcgca tcgacaactt ggtacaacaa caacgcgccc  960
tcgttctcag ccatcgaggc cgccgtgatc cgttcaccgc acctcctgga cttcctggag  1020
aaggttacca tctactccct cttgtctcgc tggagtaata ctcagtacat gaacatgtgg  1080
ggaggacatc gcctcgaatc tcgaccgatt ggcggcgcgc ttaacacatc cacacagggc  1140
```

```
tccacgaaca ccagcatcaa cccggtgacg ttgcaattca cttcacgcga tgtctatcgg  1200
accgagagct gggctggcct gaacctgttc ctaactcagc ccgtgaacgg tgtgcccaga  1260
gtcgatttcc actggaaatt cgtcactcat cccatcgcca gcgacaactt ctactaccca  1320
ggctacgccg gtatcggcac acagcttcaa gactccgaga acgaactgcc tcccgagact  1380
actggccagc cgaactacga gagttactcc cataggcttt cgcacatcgg cctaatctca  1440
gcttcgcatg ttaaagcact cgtgtactca tggacacaca gaagcgccga cagaacgaac  1500
accattgagc caaactctat cacgcagatc ccgctggtta aggcgttcaa cttgtcgagc  1560
ggcgctgcgg tcgtgcgcgg acctggattc accggtggcg acattctgcg ccgcaccaac  1620
acaggaacct tcggcgacat ccgggtgaac atcaacccgc cgtttgcaca acgctatcgc  1680
gtcaggatac ggtacgcatc cacgacggac ctccagttcc acaccagcat caacgggaag  1740
gctatcaacc agggaaactt tagcgccacg atgaaccgtg gtgaggactt ggactacaag  1800
acattccgga cggtcggctt cacgacgccc ttcagcttta gcgacgtcca gtccaccttc  1860
accatcggag catggaactt cagtagcggc aacgaggtgt acatcgaccg aatcgagttc  1920
gtcccggttg aggtgaccta cggagccgaa tacgacttcg agaagtga              1968
```

```
SEQ ID NO: 13          moltype = AA  length = 674
FEATURE                Location/Qualifiers
REGION                 1..674
                       note = An amino acid sequence of the variant TIC2199_1
                        variant with the initiating methionine removed and used to
                        operably link to a chloroplast transit peptide.
source                 1..674
                       mol_type = protein
                       organism = synthetic construct
SEQUENCE: 13
SKYKNVAPFV SASTIQTGIG IAGKILGTLG VPFAGQIASL YSFILGELWP KGKSQWEIFM  60
EHVEEIINQK ISTYARNKAL SDLRGLGDAL AVYHESLESW VENRNNTRAR SVVKNQYIAL  120
ELMFVQKLPS FAVSGEEVPL LPIYAQAANL HLLLLRDVSI FGKEWGLSAS EISTFYNRQV  180
ERTRDYSDHC VKWYNTGLNN LRGTNAKSWV RYNQFRKDMT LMVLDLVALF PSYDTLVYPI  240
KTTSQLTREV YTDAIGTVHP NQAFASTTWY NNNAPSFSAI EAAVIRSPHL LDFLEKVTIY  300
SLLSRWSNTQ YMNMWGGHRL ESRPIGGALN TSTQGSTNTS INPVTLQFTS RDVYRTESWA  360
GLNLFLTQPV NGVPRVDFHW KFVTHPIASD NFYYPGYAGI GTQLQDSENE LPPETTGQPN  420
YESYSHRLSH IGLISASHVK ALVYSWTHRS ADRTNTIEPN SITQIPLVKA FNLSSGAAVV  480
RGPGFTGGDI LRRTNTGTFG DIRVNINPPF AQRYRVRIRY ASTTDLQFHT SINGKAINQG  540
NFSATMNRGE DLDYKTFRTV GFTTPFSFSD VQSTFTIGAW NFSSGNEVYI DRIEFVPVEV  600
TYGAEYDFEK AQEKVTALFT STNPRELKID VTDYHIDQVS NLVESLLDEF YLDEKRELFE  660
IVKYAKQLYI ERNM                                                   674
```

```
SEQ ID NO: 14          moltype = DNA  length = 2025
FEATURE                Location/Qualifiers
misc_feature           1..2025
                       note = A synthetic coding sequence encoding the TIC2199_1
                        variant with the initiating methionine codon removed and
                        used to operably link to a chloroplast transit peptide,
                        and capable of use in a plant cell.
source                 1..2025
                       mol_type = other DNA
                       organism = synthetic construct
SEQUENCE: 14
tctaagtaca agaacgtcgc acccttcgtc tcggcttcta cgatccagac gggcattggc  60
atcgccggga agatactcgg cacactcggc gtcccgttcg ctggtcaaat cgcctcgctc  120
tactccttca tactcggtga actgtggccg aagggcaagt cgcagtggga aatcttcatg  180
gagcacgtgg aggagatcat caaccagaag ataagcacct acgcccgtaa caaggcgctg  240
agcgacctcc gtgggctggg cgatgcgctg gcggtgtacc acgagtcgct ggagtcgtgg  300
gtggagaacc gcaacaacac ccgcgcccgg tccgtggtca agaaccagta cattgccctg  360
gagctgatgt tcgtgcagaa gctcccgtcc ttcgcggtgt ccggcgagga agtgccactg  420
ttgcccatct acgcccaagc agccaacctg cacctccttc tcctccggga cgtcagcatc  480
ttcgggaagg agtggggcct ttcagcgtca gagatttcaa ccttctacaa caggcaagtt  540
gagcgcacgc gcgactactc ggaccactgc gtcaagtggt acaacaccgg cctcaacaac  600
ctgcgtggaa cgaacgccaa gagctgggtc cgctacaacc agtttcgaaa ggacatgacc  660
ctcatggtgc tggaccttgt ggccttgttc ccgtcctacg acaccctcgt ttatccgatt  720
aagactacat ctcaacttac ccgcgaggtt tacacagacg ccatagggac cgtgcatcct  780
aaccaggcgt tcgcatcgac aacttggtac aacaacaacg cgccctcgtt ctcagccatc  840
gaggccgccg tgatccgttc accgcacctc ctggacttcc tggagaaggt taccatctac  900
tccctcttgt ctcgctggag taatactcag tacatgaaca tgtggggagg acatcgcctc  960
gaatctcgac cgattggcgg cgcgcttaac acatccacac agggctccac gaacaccagc  1020
atcaacccgg tgacgttgca attcacttca cgcgatgtct atcggaccga gagctgggct  1080
ggcctgaacc tgttcctaac tcagcccgtg aacggtgtgc ccagagtcga tttccactgg  1140
aaattcgtca ctcatcccat cgccagcgac aacttctact acccaggcta cgccggtatc  1200
ggcacacagc ttcaagactc cgagaacgaa ctgcctcccg agactactgg ccagccgaac  1260
tacgagagtt actcccatag gctttcgcac atcggcctaa tctcagcttc gcatgttaaa  1320
gcactcgtgt actcatggac acacagaagc gccgacagaa cgaacaccat tgagccaaac  1380
tctatcacgc agatcccgct ggttaaggcg ttcaacttgt cgagcggcgc tgcggtcgtg  1440
cgcggacctg gattcaccgg tggcgacatt ctgcgccgca ccaacacagg aaccttcggc  1500
gacatccggg tgaacatcaa cccgccgttt gcacaacgct atcgcgtcag gatacggtac  1560
gcatccacga cggacctcca gttccacacc agcatcaacg ggaaggctat caaccaggga  1620
aactttagcg ccacgatgaa ccgtggtgag gacttggact acaagacatt ccggacggtc  1680
ggcttcacga cgcccttcag ctttagcgac gtccagtcca ccttcaccat cggagcatgg  1740
aacttcagta gcggcaacga ggtgtacatc gaccgaatcg agttcgtccc ggttgaggtg  1800
```

-continued

```
acctacggag ccgaatacga cttcgagaag gcacaggaga aggtgactgc tctgtttaca  1860
agcacaaatc ctcgggaact aaagatcgac gtcacagact accacatcga ccaagttagc  1920
aacctcgtcg agagcctcct ggacgagttc tatttggacg agaagcggga gctgttcgag  1980
atcgtgaaat acgccaagca gttgtacatc gagcgtaaca tgtga                 2025

SEQ ID NO: 15          moltype = AA  length = 654
FEATURE                Location/Qualifiers
REGION                 1..654
                       note = An amino acid sequence of the variant TIC2199_2
                        variant with the initiating methionine removed and used to
                        operably link to a chloroplast transit peptide.
source                 1..654
                       mol_type = protein
                       organism = synthetic construct
SEQUENCE: 15
KPKNQNMYQS LSSNVTVDKI STNPLKNETD IELQNINHEA CLKMSKYKNV APFVSASTIQ  60
TGIGIAGKIL GTLGVPFAGQ IASLYSFILG ELWPKGKSQW EIFMEHVEEI INQKISTYAR  120
NKALSDLRGL GDALAVYHES LESWVENRNN TRARSVVKNQ YIALELMFVQ KLPSFAVSGE  180
EVPLLPIYAQ AANLHLLLLR DVSIFGKEWG LSASEISTFY NRQVERTRDY SDHCVKWYNT  240
GLNNLRGTNA KSWVRYNQFR KDMTLMVLDL VALFPSYDTL VYPIKTTSQL TREVYTDAIG  300
TVHPNQAFAS TTWYNNNAPS FSAIEAAVIR SPHLLDFLEK VTIYSLLSRW SNTQYMNMWG  360
GHRLESRPIG GALNTSTQGS TNTSINPVTL QFTSRDVYRT ESWAGLNLFL TQPVNGVPRV  420
DFHWKFVTHP IASDNFYYPG YAGIGTQLQD SENELPPETT GQPNYESYSH RLSHIGLISA  480
SHVKALVYSW THRSADRTNT IEPNSITQIP LVKAFNLSSG AAVVRGPGFT GGDILRRTNT  540
GTFGDIRVNI NPPFAQRYRV RIRYASTTDL QFHTSINGKA INQGNFSATM NRGEDLDYKT  600
FRTVGFTTPF SFSDVQSTFT IGAWNFSSGN EVYIDRIEFV PVEVTYGAEY DFEK        654

SEQ ID NO: 16          moltype = DNA  length = 1965
FEATURE                Location/Qualifiers
misc_feature           1..1965
                       note = A synthetic coding sequence encoding the TIC2199_2
                        variant with the initiating methionine codon removed and
                        used to operably link to a chloroplast transit peptide,
                        and capable of use in a plant cell.
source                 1..1965
                       mol_type = other DNA
                       organism = synthetic construct
SEQUENCE: 16
aagcccaaga atcagaacat gtaccagtcc ctcagctcga acgtcaccgt cgataagatt  60
agcaccaacc cgctcaagaa tgagaccgac atcgaattac agaacattaa ccacgaggcg  120
tgcctcaaga tgtctaagta caagaacgtc gcacccttcg tctcggcttc tacgatccag  180
acgggcattg gcatcgccgg gaagatactc ggcacactcg gcgtcccgtt cgctggtcaa  240
atcgcctcgc tctactcctt catactcggt gaactgtggc cgaagggcaa gtcgcagtgg  300
gaaatcttca tggagcacgt ggaggagatc atcaaccaga agataagcac ctacgcccgt  360
aacaaggcgc tgagcgacct ccgtgggctg ggcgatgcgc tggcggtgta ccacgagtcg  420
ctggagtcgt gggtggagaa ccgcaacaac acccgcgccc ggtccgtggt caagaaccag  480
tacattgccc tggagctgat gttcgtgcag aagctcccgt ccttcgcggt gtccggcgag  540
gaagtgccac tgttgcccat ctacgcccaa gcagccaacc tgcacctcct tctcctccgg  600
gacgtcagca tcttcgggaa ggagtggggc ctttcagcgt cagagatttc aaccttctac  660
aacaggcaag ttgagcgcac gcgcgactac tcggaccact gcgtcaagtg gtacaacacc  720
ggcctcaaca acctgcgtgg aacgaacgcc aagagctggg tccgctacaa ccagtttcga  780
aaggacatga ccctcatggt gctggacctt gtggccttgt tcccgtccta cgacaccctc  840
gtttatccga ttaagactac atctcaactt acccgcgagg tttacacaga cgccataggg  900
accgtgcatc ctaaccaggc gttcgcatcg acaacttggt acaacaacaa cgcgccctcg  960
ttctcagcca tcgaggccgc cgtgatccgt tcaccgcacc tcctggactt cctggagaag  1020
gttaccatct actccctctt gtctcgctgg agtaatactc agtacatgaa catgtgggga  1080
ggacatcgcc tcgaatctcg accgattggc ggcgcgctta acacatccac acagggctcc  1140
acgaacacca gcatcaaccc ggtgacgttg caattcactt cacgcgatgt ctatcggacc  1200
gagagctggg ctggcctgaa cctgttccta actcagcccg tgaacggtgt gcccagagtc  1260
gatttccact ggaaattcgt cactcatccc atcgccagcg acaacttcta ctacccaggc  1320
tacgccggta tcggcacaca gcttcaagac tccgagaacg aactgcctcc cgagactact  1380
ggccagccga actacgagag ttactcccat aggctttcgc acatcggcct aatctcagct  1440
tcgcatgtta aagcactcgt gtactcatgg acacacagaa gcgccgacag aacgaacacc  1500
attgagccaa actctatcac gcagatcccg ctggttaagg cgttcaactt gtcgagcggc  1560
gctgcggtcg tgcgcggacc tggattcacc ggtggcgaca ttctgcgccg caccaacaca  1620
ggaaccttcg gcgacatccg ggtgaacatc aacccgccgt ttgcacaacg ctatcgcgtc  1680
aggatacggt acgcatccac gacggacctc cagttccaca ccagcatcaa cgggaaggct  1740
atcaaccagg gaaactttag cgccacgatg aaccgtggtg aggacttgga ctacaagaca  1800
ttccggacgg tcggcttcac gacgcccttc agctttagcg acgtccagtc caccttcacc  1860
atcggagcat ggaacttcag tagcggcaac gaggtgtaca tcgaccgaat cgagttcgtc  1920
ccggttgagg tgacctacgg agccgaatac gacttcgaga agtga                 1965

SEQ ID NO: 17          moltype = AA  length = 610
FEATURE                Location/Qualifiers
REGION                 1..610
                       note = An amino acid sequence of the variant TIC2199_3
                        variant with the initiating methionine removed and used to
                        operably link to a chloroplast transit peptide.
```

-continued

```
source                  1..610
                        mol_type = protein
                        organism = synthetic construct
SEQUENCE: 17
SKYKNVAPFV SASTIQTGIG IAGKILGTLG VPFAGQIASL YSFILGELWP KGKSQWEIFM  60
EHVEEIINQK ISTYARNKAL SDLRGLGDAL AVYHESLESW VENRNNTRAR SVVKNQYIAL  120
ELMFVQKLPS FAVSGEEVPL LPIYAQAANL HLLLLRDVSI FGKEWGLSAS EISTFYNRQV  180
ERTRDYSDHC VKWYNTGLNN LRGTNAKSWV RYNQFRKDMT LMVLDLVALF PSYDTLVYPI  240
KTTSQLTREV YTDAIGTVHP NQAFASTTWY NNNAPSFSAI EAAVIRSPHL LDFLEKVTIY  300
SLLSRWSNTQ YMNMWGGHRL ESRPIGGALN TSTQGSTNTS INPVTLQFTS RDVYRTESWA  360
GLNLFLTQPV NGVPRVDFHW KFVTHPIASD NFYYPGYAGI GTQLQDSENE LPPETTGQPN  420
YESYSHRLSH IGLISASHVK ALVYSWTHRS ADRTNTIEPN SITQIPLVKA FNLSSGAAVV  480
RGPGFTGGDI LRRTNTGTFG DIRVNINPPF AQRYRVRIRY ASTTDLQFHT SINGKAINQG  540
NFSATMNRGE DLDYKTFRTV GFTTPFSFSD VQSTFTIGAW NFSSGNEVYI DRIEFVPVEV  600
TYGAEYDFEK                                                         610

SEQ ID NO: 18           moltype = DNA  length = 1833
FEATURE                 Location/Qualifiers
misc_feature            1..1833
                        note = A synthetic coding sequence encoding the TIC2199_3
                         variant with the initiating methionine codon removed and
                         used to operably link to a chloroplast transit peptide,
                         and capable of use in a plant cell.
source                  1..1833
                        mol_type = other DNA
                        organism = synthetic construct
SEQUENCE: 18
tctaagtaca agaacgtcgc acccttcgtc tcggcttcta cgatccagac gggcattggc  60
atcgccggga agatactcgg cacactcggc gtcccgttcg ctggtcaaat cgcctcgctc  120
tactccttca tactcggtga actgtggccg aagggcaagt cgcagtggga aatcttcatg  180
gagcacgtgg aggagatcat caaccagaag ataagcacct acgcccgtaa caaggcgctg  240
agcgacctcc gtgggctggg cgatgcgctg gcggtgtacc acgagtcgct ggagtcgtgg  300
gtggagaacc gcaacaacac ccgcgcccgg tccgtggtca agaaccagta cattgccctg  360
gagctgatgt tcgtgcagaa gctcccgtcc ttcgcggtgt ccggcgagga agtgccactg  420
ttgcccatct acgcccaagc agccaacctg cacctccttc tcctccggga cgtcagcatc  480
ttcgggaagg agtggggcct ttcagcgtca gagatttcaa ccttctacaa caggcaagtt  540
gagcgcacgc gcgactactc ggaccactgc gtcaagtggt acaacaccgg cctcaacaac  600
ctgcgtggaa cgaacgccaa gagctgggtc cgctacaacc agtttcgaaa ggacatgacc  660
ctcatggtgc tggaccttgt ggccttgttc ccgtcctacg acaccctcgt ttatccgatt  720
aagactacat ctcaacttac ccgcgaggtt tacacagacg ccatagggac cgtgcatcct  780
aaccaggcgt tcgcatcgac aacttggtac aacaacaacg cgccctcgtt ctcagccatc  840
gaggccgccg tgatccgttc accgcacctc ctggacttcc tggagaaggt taccatctac  900
tccctcttgt ctcgctggag taatactcag tacatgaaca tgtggggagg acatcgcctc  960
gaatctcgac cgattggcgg cgcgcttaac acatccacac agggctccac gaacaccagc  1020
atcaacccgg tgacgttgca attcacttca cgcgatgtct atcggaccga gagctgggct  1080
ggcctgaacc tgttcctaac tcagcccgtg aacggtgtgc ccagagtcga tttccactgg  1140
aaattcgtca ctcatcccat cgccagcgac aacttctact acccaggcta cgccggtatc  1200
ggcacacagc ttcaagactc cgagaacgaa ctgcctcccg agactactgg ccagccgaac  1260
tacgagagtt actcccatag gctttcgcac atcggcctaa tctcagcttc gcatgttaaa  1320
gcactcgtgt actcatggac acacagaagc gccgacagaa cgaacaccat tgagccaaac  1380
tctatcacgc agatcccgct ggttaaggcg ttcaacttgt cgagcggcgc tgcggtcgtg  1440
cgcggacctg gattcaccgg tggcgacatt ctgcgccgca ccaacacagg aaccttcggc  1500
gacatccggg tgaacatcaa cccgccgttt gcacaacgct atcgcgtcag gatacggtac  1560
gcatccacga cggacctcca gttccacacc agcatcaacg ggaaggctat caaccaggga  1620
aactttagcg ccacgatgaa ccgtggtgag gacttggact acaagacatt ccggacggtc  1680
ggcttcacga cgcccttcag ctttagcgac gtccagtcca ccttcaccat cggagcatgg  1740
aacttcagta gcggcaacga ggtgtacatc gaccgaatcg agttcgtccc ggttgaggtg  1800
acctacggag ccgaatacga cttcgagaag tga                               1833
```